US012594258B2

(12) United States Patent
Sherman et al.

(10) Patent No.: US 12,594,258 B2
(45) Date of Patent: Apr. 7, 2026

(54) INHIBITORS OF MHC-I NEF DOWNMODULATION FOR TREATING HIV

(71) Applicant: THE REGENTS OF THE UNIVERSITY OF MICHIGAN, Ann Arbor, MI (US)

(72) Inventors: David H. Sherman, Ann Arbor, MI (US); Kathleen L. Collins, Ann Arbor, MI (US); Andrew W. Robertson, Ann Arbor, MI (US); Mark M. Painter, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 735 days.

(21) Appl. No.: 17/785,809

(22) PCT Filed: Dec. 16, 2020

(86) PCT No.: PCT/US2020/065260
§ 371 (c)(1),
(2) Date: Jun. 15, 2022

(87) PCT Pub. No.: WO2021/126942
PCT Pub. Date: Jun. 24, 2021

(65) Prior Publication Data

US 2023/0088583 A1 Mar. 23, 2023

Related U.S. Application Data

(60) Provisional application No. 62/948,646, filed on Dec. 16, 2019.

(51) Int. Cl.
*C07H 19/048* (2006.01)
*A61K 31/366* (2006.01)
*A61K 31/7048* (2006.01)
*A61P 31/18* (2006.01)

(52) U.S. Cl.
CPC ........ *A61K 31/366* (2013.01); *A61K 31/7048* (2013.01); *A61P 31/18* (2018.01)

(58) Field of Classification Search
CPC .... A61K 31/7048; A61K 31/366; A61P 31/18
See application file for complete search history.

(56) References Cited

FOREIGN PATENT DOCUMENTS

WO WO-93/04055 A2 3/1993
WO WO-2017/151586 A1 9/2017

OTHER PUBLICATIONS

Kinashi. The Journal of Antibiotics. vol. 35 Issue 11 pp. 1618-1620 (Year: 1982).*
Schaeffer. Journal of Virology, Feb. 2004. pp. 1375-1383. (Year: 2004).*
Lou. Journal of Virology, Mar. 1996, p. 1527-1534 (Year: 1996).*
Li. Scientific Reports, 7, 4024, Jan. 2017 (Year: 2017).*
Weintraub. Scientific American. First New HIV Strain in 19 Years Identified. Nov. 2019. (Year: 2019).*
Gagliardi. J. Med. Chem. 1998, 41, 1883-1893. (Year: 1998).*
Kuate et al. Virology 351 (2006) 133-144. (Year: 2006).*
Berge et al., Pharmaceutical Salts, Journal of Pharmaceutical Sciences, 66, 1-19 (Jan. 1977).
Fredericksen et al., Inhibition of endosomal/lysosomal degradation increases the infectivity of human immunodeficiency virus, J. Virol., 76(22):11440-6 (Nov. 2002).
International Application No. PCT/US2020/065260, International Search Report and Written Opinion, Mar. 29, 2021.
Larsen et al., The Merrifield peptide synthesis studied by near-infrared Fourier-transform Raman spectroscopy, J. Am. Chem. Soc., 115(14):6247-6253 (1993).
Luo et al., Inhibition of Nef- and phorbol ester-induced CD4 degradation by macrolide antibiotics, J. Virol., 70(3):1527-34 (Mar. 1996).
Merrifield, "Solid Phase Peptide Synthesis. I. The Synthesis of a Tetrapeptide," J Am Chem Soc 85:2149-2154 (1963).
O'Donnell et al., Solid-phase unnatural peptide synthesis (UPS), J. Am. Chem. Soc., 118: 6070-6071 (1996).
Painter et al., Concanamycin A counteracts HIV-1 Nef to enhance immune clearance of infected primary cells by cytotoxic T lymphocytes, Proc. Natl. Acad. Sci. USA, 117(38):23835-46 (Sep. 2020).
Smith et al., Solid-phase peptide synthesis and biological activity of bovine thymopoietin II (bTP-II), Int. J. Peptide Protein Res., 44:183 (1994).
Erickson et al., Solid-phase peptide synthesis, IN: The Proteins, 3rd ed., 2: 257-527 (1976).
Finn et al., The synthesis of peptides by solution methods with emphasis on peptide hormones, IN: The Proteins, 3rd ed., 2: 105-253 (1976).
Stewart et al., *Solid Phase Peptide Synthesis*, San Francisco: W.H. Freeman and Company (1969).

* cited by examiner

*Primary Examiner* — Scarlett Y Goon
*Assistant Examiner* — Samantha Lynn Schachermeyer
(74) *Attorney, Agent, or Firm* — MARSHALL, GERSTEIN & BORUN LLP

(57) ABSTRACT

Provided herein are compounds that can inhibit MHC-I downmodulation, and treat HIV infection in a patient in need of treatment thereof.

18 Claims, 15 Drawing Sheets

INHIBITORS OF MHC-I NEF DOWNMODULATION FOR TREATING HIV

STATEMENT OF GOVERNMENTAL INTEREST

This invention was made with government support under AI116158, AI148383 and AI131957 awarded by the National Institutes of Health. The government has certain rights in the invention.

CROSS REFERENCE TO RELATED APPLICATIONS

This Application is a U.S. National Stage of International Patent Application No. PCT/US20/65260 filed Dec. 16, 2020, which claims the benefit of priority of USSN 62/948,646 filed Dec. 16, 2019, the respective disclosures of which are each incorporated herein by reference in their entireties.

FIELD

This disclosure relates generally to inhibitors of MHC-I downmodulation, and methods of treating or preventing an HIV infection by administering the inhibitors to a patient in need of treatment thereof.

BACKGROUND

Nef is an accessory protein encoded by Human Immunodeficiency Virus (HIV) responsible for the downmodulation of major histocompatibility complex class proteins (MHC-I), masking infection from the host immune system and allowing HIV infected cells to persist. Current treatment, utilizing combined antiretroviral therapies (cART), suppresses viral levels in the blood, but does not eradicate reservoirs of cells harboring integrated copies of latent HIV genomes. Approaches to clear reservoirs by reactivating infected cells have provided evidence that latency can be reversed in vivo, however, studies thus far suggest that this approach alone will not decrease cellular reservoirs. A medication capable of reversing Nef-mediated downmodulation of MHC-I could promote eradication of HIV-infection utilizing the host immune system, a long-sought objective of anti-HIV therapy.

Thus, there is still a need for drugs for treating HIV infections, such as drugs which decrease or eliminate the viral reservoir in patients by e.g., inhibiting Nef-mediated downmodulation of MHC-I.

SUMMARY

The present disclosure generally relates to methods of treating HIV, to methods of inhibiting the replication of HIV viruses, to methods of reducing the amount of HIV viruses, to compounds and compositions that can be employed for such methods.

In one aspect, the disclosure provides compounds of Formula I and pharmaceutically acceptable salts thereof:

(I)

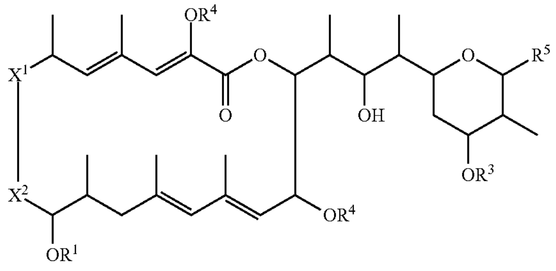

wherein

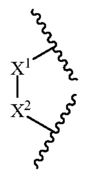

is

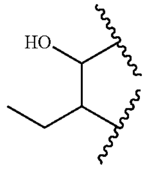

or represents a direct bond, $R^1$ is H, $C(O)R^6$, or a sugar moiety, $R^2$ is H or OH, $R^3$ is H, $C(O)R^7$ or a sugar moiety, each $R^4$ is independently H or $C_{1-6}$alkyl, $R^5$ is $C_{1-6}$alkyl or $C_{2-6}$alkenyl, and $R^6$ and $R^7$ are each independently $C_{1-6}$ alkyl.

In some cases, the compounds are compounds of Formula Ia or Ib:

(Ia)

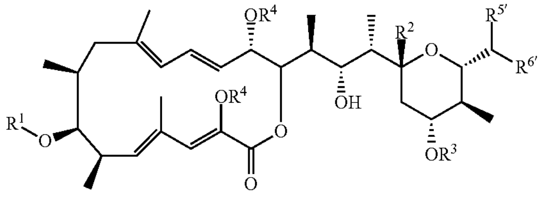

or (Ib)

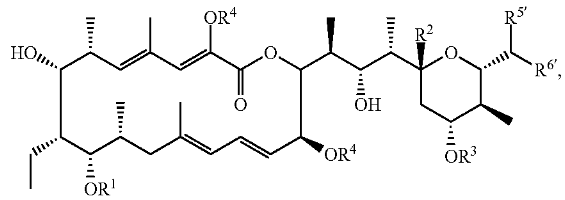

wherein $R^{5'}$ is $C_{1-5}$alkyl or $C_{2-5}$alkenyl and $R^{6'}$ is $C_{1-5}$alkyl. In some cases, the compounds are compounds of Formula II:

(II)

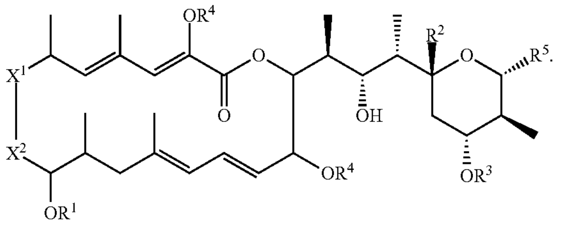

Further provided are methods of administering to a patient a safe and effective amount of a compound as disclosed herein, e.g., as represented by Formulas I, Ia, Ib, or II, or a compound of Table A.

Also provided are methods of modulating HIV Nef in a subject in need thereof by contacting said HIV Nef with a safe and effective amount of a compound as disclosed herein, e.g., as represented by Formulas I, Ia, Ib, or II, or a compound of Table A. In some cases, modulating HIV Nef includes administering to a patient a safe and effective amount of a compound as disclosed herein e.g., as represented by Formulas I, Ia, Ib, or II, or a compound of Table A.

Further provided are methods of treating an HIV Nef-associated disorder in a host by administering a safe and effective amount of a compound as disclosed herein, e.g., as represented by Formulas I, Ia, Ib, or II, or a compound of Table A.

Further provided are methods of treating HIV infection in a patient, comprising administering to said patient a safe and effective amount of a compound as disclosed herein, e.g., as represented by Formulas I, Ia, Ib, or II, or a compound of Table A.

Further provided are methods of reducing an HIV reservoir in a patient, comprising administering to said patient a safe and effective amount of a compound as disclosed herein, e.g., as represented by Formulas I, Ia, Ib, or II, or a compound of Table A. Also provided are methods of eliminating an HIV reservoir in a patient, comprising administering to said patient a safe and effective amount of a compound as disclosed herein, e.g., as represented by Formulas I, Ia, Ib, or II, or a compound of Table A.

Also provided are pharmaceutical compositions comprising a compound as disclosed herein, e.g., as represented by any of Formulas I, Ia, Ib, or II, or a compound of Table A, or a pharmaceutically acceptable salt thereof, and a pharmaceutically acceptable excipient, carrier, adjuvant or vehicle.

Further provided herein are uses of a compound described herein for the manufacture of a medicament for treating HIV infection in a patient, for reducing an HIV reservoir in a patient, or for eliminating an HIV reservoir in a patient.

BRIEF DESCRIPTION OF THE FIGURES

(FIGS. 6E-F) n=4; (FIGS. 6G-H)

DETAILED DESCRIPTION

Figure 1:
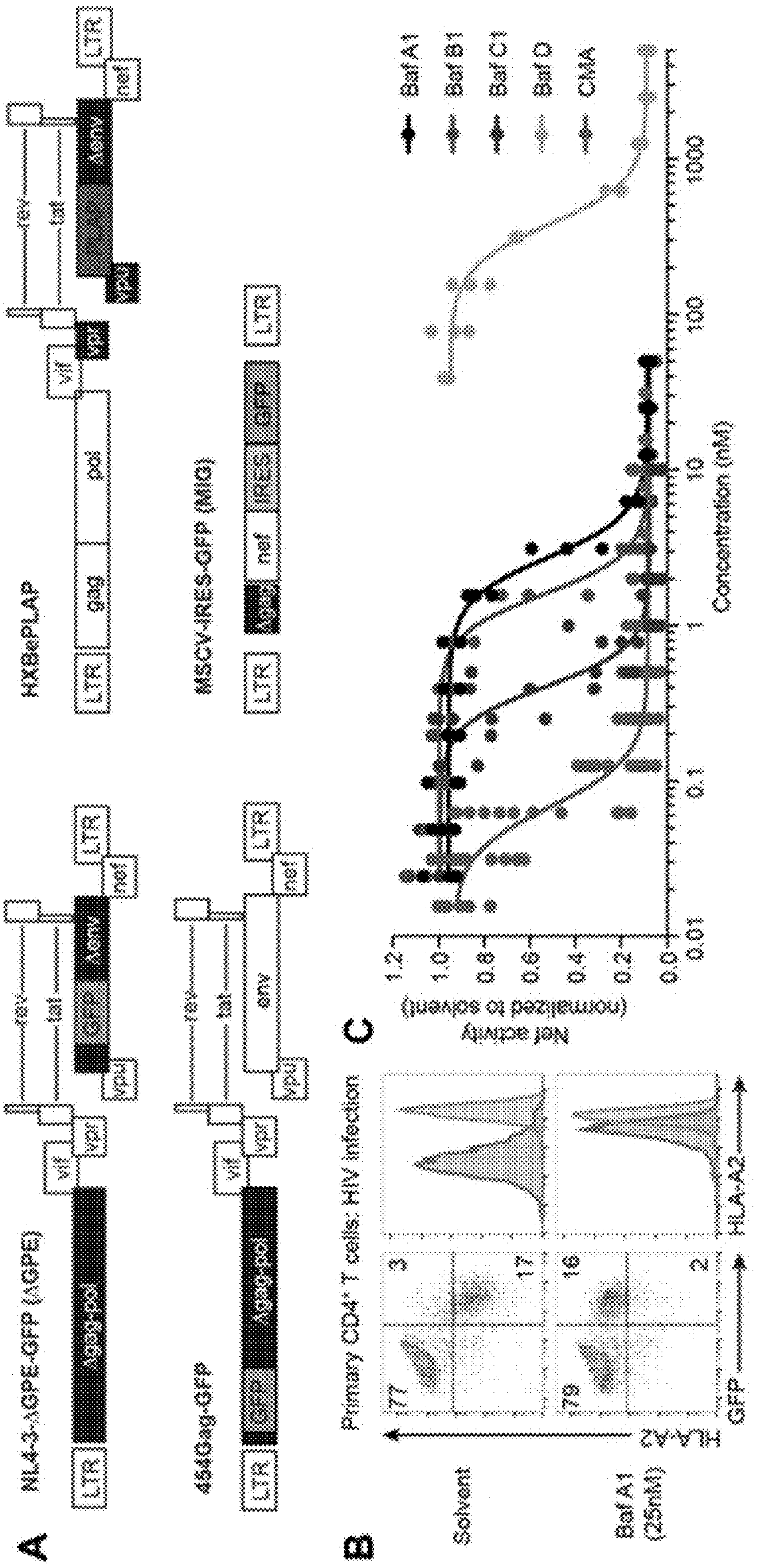
FIG. 1A is schematic representations of viral genomes as described throughout the description.
FIG. 1B is representative flow cytometry plots (n=3) from primary activated $CD4^+$ T cells infected with HIV ΔGPE and treated with Baf A1. Histograms to the left are from $GFP^-$ cells, histograms to the right are from infected $GFP^+$ cells.
FIG. 1C is a summary graph of the complied data of FIG. 1B, showing f flow cytometric data from primary $CD4^+$ T cells infected as in B and treated with the indicated plecomacrolides (n=4 for Baf A1, n=3 for Baf B1, n=8 for Baf C1 , n=3 for Baf D, n=12 for CMA).
FIG. 1D is representative flow cytometric polts from the data summarized in FIG. 1C showing Nef activity down-modulation of Nef normalized to solvent control The plots are shown from the donor with results closest to the mean among 12 donors tested. Percent restoration, fold down-modulation, and Nef activity were calculated as described in Materials and Methods.
FIG. 1E is a summary graph comparing Nef activity as in FIG. 1D after 24 hours (n=3 for Baf A1, n=8 for BafC1, n=12 for CMA) and viability after 72 hours of plecomacrolide exposure (n=3 for Baf A1 and BafC1, n=6 for CMA). Solvent control shown in the graph is DMSO. Extra sum-of-squares F test used to compare $IC_{50}$ values of curves.
Figure 1:
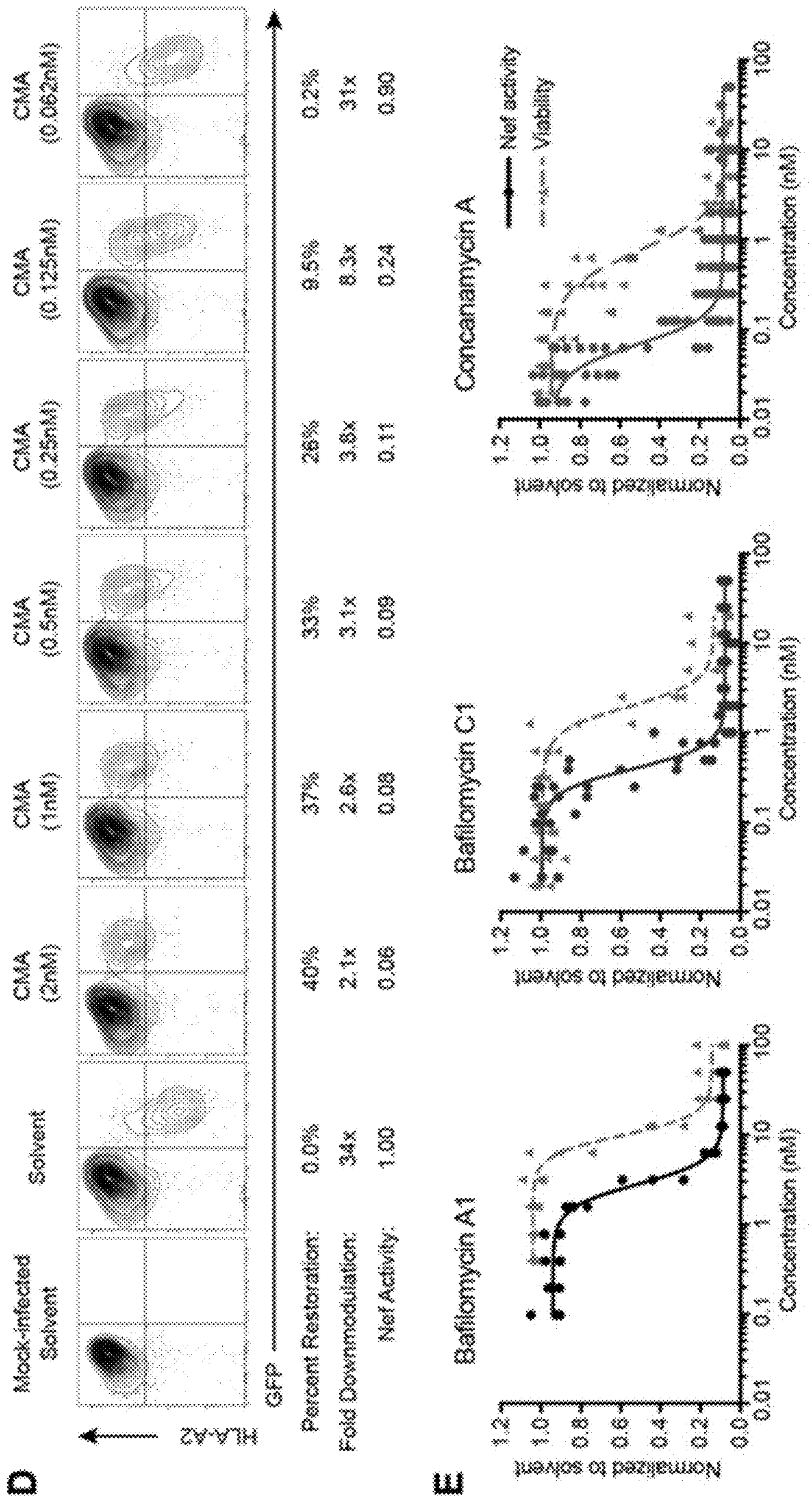

The development of combination antiretroviral therapy (ART) has drastically altered the course of the HIV epidemic, yet HIV infection remains a lifelong condition for which there is no cure. The virus persists despite the presence of HIV-specific cytotoxic T lymphocytes (CTLs), the main effectors of cellular adaptive immunity responsible for clearing viral infections. While rare elite controllers with particularly potent CTLs or CTLs targeting vulnerable antigens can spontaneously suppress the virus, even these individuals fail to clear the infection. In controllers or ART-treated patients with suppressed viral loads, HIV persists in long-lived latent reservoirs of virus. Approaches to clear these reservoirs by reactivating latent viruses have provided evidence that latency can be reversed in vivo, but this alone is unlikely to eliminate cellular reservoirs. Thus, new strategies are needed to enhance the clearance of cells harboring reactivated HIV.

CTLs recognize peptide antigens presented in the context of major histocompatibility complex class-I (MHC-I) on the surface of infected cells, mediating death of the target cell through perforin and F as lytic pathways. MHC-I is both polygenic, with genes encoding HLA-A, -B, -C, -E, -F, and -G, and polymorphic, with remarkable allelic variation particularly in HLA-A, -B, and -C. Polygeny allows for functional separation, as HLA-A and -B, and to a lesser extent -C, are responsible for presenting peptides to CTLs, which recognize non-self-antigens expressed by intracellular pathogens. HLA-C, -E, and -G are predominantly responsible for inhibiting the responsiveness of natural killer (NK) cells, which recognize targets cells with low MHC-I and elevated natural killer cell activating ligands. Allelic variation in the antigen-presenting forms of MHC-I yields alleles that are optimized for presentation of diverse peptides. Some alleles of HLA-B, in particular, are associated with rapid or delayed progression of HIV disease, and this may be attributable to whether the optimal peptide repertoire for an allele includes vulnerable regions in the HIV genome.

MHC-I is loaded with peptides in the ER and proceeds through the secretory pathway to reach the cell surface. The HIV accessory protein Nef alters MHC-I trafficking by binding to the cytoplasmic tail of MHC-I early in the secretory pathway, stabilizing an interaction between a tyrosine residue in the MHC-I cytoplasmic tail and the tyrosine-binding pocket in the μsubunit of clathrin adaptor protein 1 (AP-1). Formation of the AP-1:Nef:MHC-I complex mediates the redirection of MHC-I into the endolysosomal trafficking pathway in an ADP-ribosylation factor-1 (ARF-1)-dependent manner, where it is degraded at an accelerated rate in the lysosome. Lysosomal acidification, which is required for the function of lysosomal proteases responsible for this degradation, is maintained by the vacuolar $H^+$-ATPase (V-ATPase), a rotary proton-pumping motor. X-ray crystallography and cryo-electron microscopy analyses have confirmed the direct contacts between Nef, MHC-I, AP-1, and ARF-1 and described the structural basis for these interactions.

As a result of these interactions, HIV-infected cells expressing Nef experience a loss of cell-surface MHC-I, which protects them from killing by HIV-specific CTLs Nef binds specifically to the cytoplasmic domains of HLA-A and -B, but not HLA-C and -E. Because of their different functional roles, this differentiation optimizes evasion of both CTL and NK cell responses and is conserved across primate lentiviruses. Furthermore, the magnitude of Nef-mediated downregulation of HLA-A is greater than that of HLA-B, which may explain the observation that HLA-B-restricted CTL responses are more protective against HIV.

The identification of a potent inhibitor of Nef that restores MHC-I to the surface of HIV-infected cells therefore represents an important and perhaps essential step toward the goal of efficiently clearing HIV reservoirs. Here is described a novel function for the plecomacrolide family of natural products, in particular concanamycin A (CMA), which potently counteracts Nef downregulation of MHC-I to enhance CTL-mediated clearance of HIV-infected primary lymphocytes.

Disclosed herein are compounds, and uses of these compounds, in modulating HIV Nef, e.g., for treating an HIV Nef-related disorder. One aspect of the present disclosure is generally related to the use of the compounds described herein or pharmaceutically acceptable salts, or pharmaceutically acceptable compositions comprising such a compound or a pharmaceutically acceptable salt thereof, for inhibiting the replication of HIV in a patient, for reducing the amount of HIV viruses (reducing viral titer) in a patient, and for treating HIV in a patient. Another aspect of the present disclosure is related to the use of the compounds described herein or pharmaceutically acceptable salts, or pharmaceutically acceptable compositions comprising such a compound or a pharmaceutically acceptable salt thereof, for reducing or eliminating an HIV reservoir in a patient.

Compounds of the Disclosure

The present disclosure provides compounds of Formula I, or a pharmaceutically acceptable salt thereof:

(I)

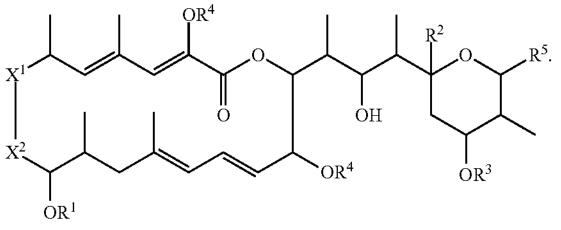

wherein

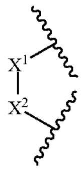

is

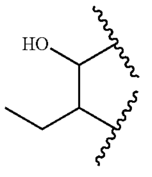

or represents a direct bond;

$R^1$ is H, $C(O)R^6$, or a sugar moiety;

$R^2$ is H or OH;

$R^3$ is H, $C(O)R^7$ or a sugar moiety;

each $R^4$ is independently H or $C_{1-6}$alkyl;

$R^5$ is $C_{1-6}$alkyl or $C_{2-6}$alkenyl; and $R^6$ and $R^7$ are each independently $C_{1-6}$ alkyl.

The term "alkyl" as used herein means a saturated straight or branched chain hydrocarbon. The term "alkenyl" as used herein means a straight or branched chain hydrocarbon comprising one or more double bonds. Each of the "alkyl" or "alkenyl" as used herein can be optionally substituted as set forth below. In some embodiments, the "alkyl" is $C_1$-$C_6$ alkyl. In some embodiments, the "alkenyl" is $C_2$-$C_6$ alkenyl.

In some cases, the compound has a structure of Formula Ia or Ib:

(Ia)

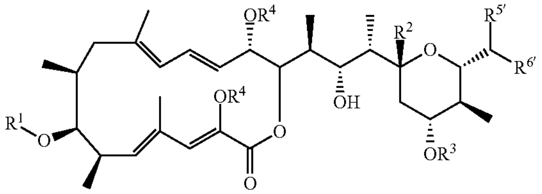

or (Ib)

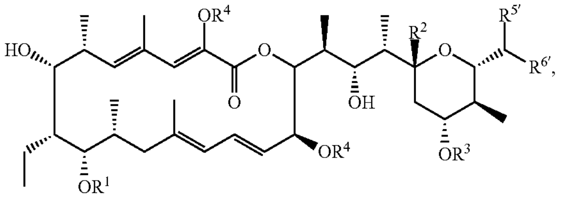

wherein $R^{5'}$ is $C_{1-5}$alkyl or $C_{2-5}$alkenyl and $R^{6'}$ is $C_{1-5}$alkyl. In some cases, the compound has a structure of Formula Ia (Ia)

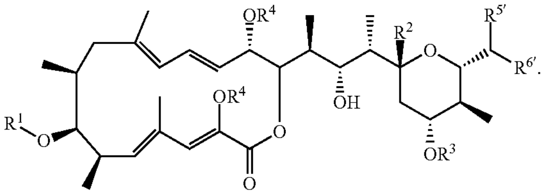

In some cases, the compound has a (Ib)

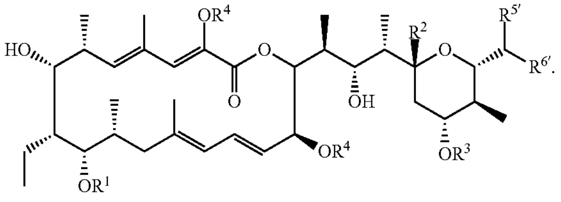

structure of Formula Ib:

In some cases, the compound has a structure of Formula II::

(II)

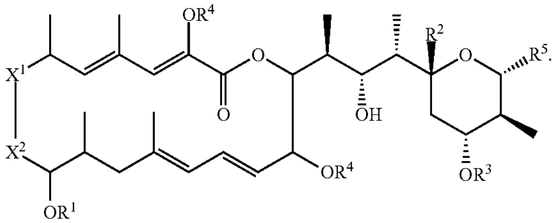

In some cases, $R^1$ is H. In some cases, $R^1$ is $C(O)R^6$. In some cases, $R^1$ is a sugar. In some cases, $R^1$ is an amino sugar.

In some cases, $R^2$ is H. In some cases, $R^2$ is OH.

In some cases, $R^3$ is H. In some cases, $R^3$ is $C(O)R^7$. In some cases, $R^3$ is a sugar. A sugar can be a pentose, hexose, heptose, or an amino sugar (e.g., aminopentose, aminohexose, aminoheptose, or a neuraminic acid), for example. Some contemplated sugars include, but are not limited to, allose, altrose, glucose, mannose, gulose, idose, galactose, talose, sialic acid, glucosamine, galactosamine, fructose, arabinose, dextrose, sorbose, psicose, tagatose, sucrose, lactose, maltose, trehalose, cellobiose, chitobiose, lactulose, kojibiose, nigerose, isomaltose, sophorose, laminaribose, gentiobiose, turanose, matlulose, plaltinose, gentiobiulose, mannobiose, melibiose, melibiulose, rutinose, rutinulose, N-acetylglucosamine, fucose, N-acetylneuraminic acid, sialic acid, xylobiose, ribose, rhamnose, xylose, cladinose, mycinose, javose, 2-deoxy-β-D-rhamnose, and the like. Contemplated amino sugars include desosamine, mycaminose, and the like. For the avoidance of doubt, the terms "carbohydrate," "sugar," and "saccharide" are all used interchangeably. In some cases, $R^3$ is an amino sugar. In some cases, $R^3$ is a carbamyl sugar (e.g., a sugar having a —OC(O)NR— moiety, where R is H or $C_{1-6}$alkyl) . In some cases, $R^3$ is

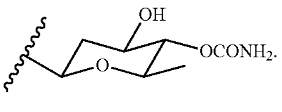

In some cases, at least one $R^4$ is $C_{1-6}$alkyl. In some cases, each $R^4$ is $C_{1-6}$alkyl. In some cases, at least one $R^4$ is methyl. In some cases, each $R^4$ is methyl.

In some cases, $R^5$ is $C_{1-6}$alkyl. In some cases, $R^5$ is $C_3$alkyl. In some cases, $R^5$ is isopropyl. In some cases, $R^5$ is $C_{2-6}$alkenyl.

In some cases, $R^{5'}$ is $C_{1-5}$alkyl. In some cases, In some cases, $R^{5'}$ is methyl. In some cases, $R^{5'}$ is $C_{2-5}$alkenyl. In some cases, $R^{5'}$ is $C_3$alkenyl. In some cases, $R^{5'}$ is allyl.

In some cases, $R^{6'}$ is H. In some cases, $R^{6'}$ is $C_{1-5}$alkyl. In some cases, $R^{6'}$ is methyl.

In some case, $R^{5'}$ is $C_{2-5}$alkenyl and $R^{6'}$ is H. In some cases, In some case, $R^{5'}$ is $C_2$alkenyl and $R^{6'}$ is H. In some cases, $R^{5'}$ and $R^{6'}$ are methyl.

As described herein, compounds described herein may optionally be substituted with one or more substituents, such as illustrated generally below, or as exemplified by particular classes, subclasses, and species described herein. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted. In some cases, the substituent is selected from group A: halo, CN, OH, $CO_2H$, CHO, $NH_2$, oxo, $NO_2$, $C_{1-6}$ alkyl, $C_{1-6}$haloalkyl, $C_{1-6}$alkoxy, $C_{1-6}$alkylthio, $C_{1-6}$alkyl-OH, $C_{3-10}$carbocyclyl, 3-7 membered heterocyclyl, $C_{3-10}$carbocyclyl-$C_{1-6}$alkoxy, $C_{3-10}$ carbocyclyl-O—$C_{1-6}$alkylene, $C_{3-10}$ carbocyclyl-$C_{1-6}$ alkoxy-$C_{1-6}$alkylene, 3-7 membered heterocyclyl-$C_{1-6}$alkoxy, 3-7 membered heterocyclyl-O-$C_{1-6}$alkylene, 3-7 membered heterocyclyl-$C_{1-6}$alkoxy-$C_{1-6}$alkylene, $C_{1-6}$haloalkoxy, $C_{1-6}$alkoxy-$C_{1-6}$alkylene, $C_{1-6}$alkoxy-$C_{1-6}$alkoxy, $C_{1-6}$alkyl-C(O)—, $C_{1-6}$alkyl-C(O)O—, $NHC_{1-6}$alkyl, $C_{1-6}$alkyl-C(O)NH—, $C_{1-6}$haloalkyl-C(O)NH, $C_{1-6}$alkyl-NHC(O)—, $C_{1-6}$alkyl-$SO_2$—, $C_{1-6}$alkyl-SO—, and $C_{1-6}$alkyl$SO_2$NH—.

Selection of substituents and combinations of substituents contemplated herein are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this disclosure, unless only one of the isomers is drawn specifically.

Therefore, single stereochemical isomers as well as enantiomeric, diastereomeric, cis/trans, conformational, and rotational mixtures of the present compounds are within the scope of the disclosure.

Unless otherwise indicated, all tautomeric forms of the compounds described herein are within the scope of the disclosure.

Additionally, unless otherwise indicated, structures depicted herein are also meant to include compounds that differ only in the presence of one or more isotopically enriched atoms. Discussion of an element is intended to include all isotopes of that element. For example, a substituent shown as a hydrogen includes where that hydrogen is in the deuterium or tritium isotope form, and a carbon atom can be present as a $^{13}$C- or $^{14}$C-carbon isotope.

It is understood that selections of values of each variable are those that result in the formation of stable or chemically feasible compounds.

The compound can be a compound as listed in Table A, or a pharmaceutically acceptable salt thereof.

TABLE A

| Compound No. | Structure |
| --- | --- |
| A1 | 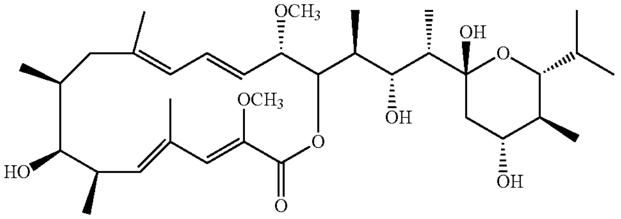 [SMILES: CO/C1=C\C(C)=C\[C@@H](C)[C@@H](O)[C@@H](C)C/C(C)=C/C=C/[C@H](OC)C([C@@H](C)[C@@H](O)[C@H](C)[C@@]2(O)C[C@@H](O)[C@H](C)[C@@H](C(C)C)O2)OC1=O] |
| A2 | 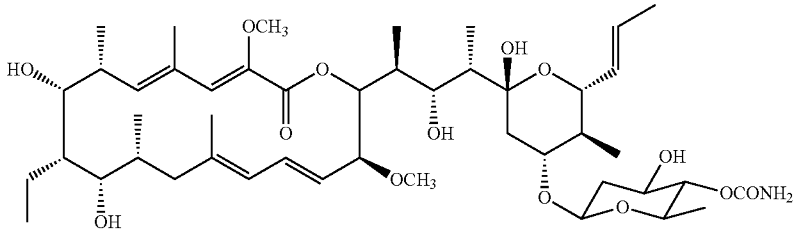 |

Methods of Use

Plecomacrolides have been identified as potent inhibitors of HIV Nef-mediated downregulation of MHC-I. Inhibition of Nef by CMA, in particular, occurs at concentrations that are non-toxic to primary T cells and that do not inhibit lysosome function. Restoration of cell-surface MHC-I in HIV-infected cells enhances their clearance by CTLs comparably to genetic deletion of Nef, confirming that the restored MHC-I is functional for presentation of viral antigens. CMA inhibits nef alleles isolated from diverse clades of HIV, an allele of SIV nef and an allele of HIV nef from an optimally-treated patient. Additionally, CMA restores diverse forms of MHC-I in HIV-infected cells, and that all combinations of nef alleles and MHC-I alleles tested result in enhanced antigen presentation with CMA treatment. Inhibition of Nef by this mechanism could have broad clinical utility.

The identification of plecomacrolides as inhibitors of HIV Nef may seem intuitive, given that Nef redirects many of its targets for lysosomal degradation and plecomacrolides lead to potent lysosomal neutralization and loss of degradative capacities. However, CMA restored MHC-I in Nef-expressing primary human $CD4^+$ T cells at concentrations that were non-toxic and did not alter the function of the lysosome or reduce the abundance of acidified intracellular compartments. Thus, CMA specifically alters an activity needed at a step prior to lysosomal degradation. This is an unrecognized activity of the known target, V-ATPase, or the activity of a novel non-V-ATPase target. Inhibition of this putative target activity leads to a reduction in the capacity of Nef to interact with MHC-I and AP-1 in CMA-treated cells but does not alter the ability of Nef to downregulate and degrade CD4. Plecomacrolides have previously been shown to alter intracellular trafficking, but with the effect of reducing the expression of cell-surface markers. The identification of a CMA-sensitive pathway that leads to increased cell-surface expression of a cellular protein appears to be unprecedented.

In short-term co-cultures with HIV-specific CTLs, primary $CD4^+$ T cells infected with Nef-expressing HIV revealed a residual population of infected cells that could not be cleared from the culture, regardless of how many CTLs were present. If the cells were treated with CMA or Nef was genetically removed from the virus, this population was virtually non-existent. This raises the possibility that Nef activity in a subset of HIV-infected cells in vivo renders those cells refractory to killing even by highly responsive CTLs. Following therapeutic reactivation in a "shock and kill" effort to eliminate the HIV reservoir, such cells could escape CTL killing long enough to proliferate and return to latency, re-seeding the reservoir with clonally-expanded sequences expressing potent alleles of nef. These co-culture assays demonstrate proof-of-concept that therapeutic Nef inhibition with low-dose CMA is sufficient to dramatically enhance the clearance of previously hard-to-kill cells when effective CTLs are present.

The CTL response in vivo is polyclonal, with CTLs responding to a diverse array of HIV antigens presented predominantly by HLA-A and HLA-B. Furthermore, MHC-I is remarkably polymorphic and HIV sequences are tremendously diverse both within and between infected individuals. A CTL-based therapeutic intervention will therefore need to function in a wide range of immune contexts. CTL responses restricted to HLA-B are predominant in HIV infection, and the MHC-I genes associated with HIV control are all HLA-B alleles (30-34). This may be explained by the observation that Nef downregulates HLA-A to a greater magnitude than HLA-B, which has been observed in investigations of HIV-infected primary cells. Nevertheless, partial reversal of Nef downregulation of diverse forms of MHC-I occurs following CMA treatment, including both HLA-A and HLA-B allotypes. Restoration was particularly dramatic when MHC-I was targeted most strongly by Nef. Therefore, CMA could enhance the efficiency of already-effective HLA-B-restricted CTL responses while enabling previously-ineffective HLA-A-restricted responses to eliminate resistant reservoirs of virus. In combination with vaccination strategies to increase the abundance and breadth of HIV-specific CTLs, antigens presented by HLA-A that are no longer hidden by Nef could become new targets that had not been under strong selective pressure to generate CTL-escape mutants prior to the initiation of ART.

In addition, the potency of CMA is greater than previously published Nef inhibitors, including B9 and lovastatin. B9 failed to restore MHC-I to the surface of Nef-expressing cells to any degree in any assay, while lovastatin was able to restore MHC-I to a fraction of the levels achieved by CMA with prolonged incubations and supratherapeutic concentrations. The explanation for the negative result obtained with B9 is unclear. Any potential effect of B9 on MHC-I downregulation in cells is not biologically meaningful under the conditions of our assays.

CMA potently counteracts HIV Nef to restore immune-mediated clearance of HIV-infected cells at subnanomolar concentrations, with the potential to broadly enhance anti-HIV immunity in diverse immune contexts. CMA shows promise as a clinical inhibitor of HIV Nef to aid in the efforts to eradicate residual HIV reservoirs as a crucial component of a cure strategy for HIV.

The compounds described herein or pharmaceutically acceptable salts thereof can be used to modulate an HIV Nef. Modulating an HIV Nef includes inhibiting an HIV Nef.

The term "HIV Nef-associated disorder" is used herein to mean diseases or disorders whose status or progression is influenced by the expression of HIV Nef in a patient. A non-limiting example of an HIV Nef-associated disorder is HIV infection, e.g., HIV-1 infection.

As used herein, "HIV" refers to the human immunodeficiency virus. HIV includes, without limitation, HIV-1. HIV-1 includes but is not limited to extracellular virus particles and the forms of HIV-1 associated with HIV-1 infected cells. The human immunodeficiency virus (HIV) may be either of the two known types of HIV (HIV-1 or HIV-2). As used herein, HIV-1 refers to any of the known major subtypes (classes A, B, C, D, E, F, G, H, or J), outlying subtype (Group O), yet to be determined subtypes of HIV-1, and recombinations thereof.

As used herein, "HIV infection" refers to infection of a subject with HIV.

The terms, "disease", "disorder", and "condition" may be used interchangeably herein to refer to an HIV Nef-associated medical or pathological condition, such as HIV infection.

As used herein, the terms "subject", "host", and "patient" are used interchangeably. The terms "subject", "host", and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, or mouse) and a primate (e.g., a monkey, chimpanzee, or human), and more specifically a human. In some embodiments, the subject is a non-human animal such as a farm animal (e.g., a horse, cow, pig or sheep), or a pet (e.g., a dog, cat, guinea pig or rabbit). In a preferred embodiment, the subject is a "human".

As used herein, the terms "treat", "treatment," and "treating" refer to both therapeutic and prophylactic treatments. For example, therapeutic treatments include the reduction or amelioration of the progression, severity and/or duration of HIV infection, or the amelioration of one or more symptoms (specifically, one or more discernible symptoms) of HIV infection, resulting from the administration of one or more therapies (e.g., one or more therapeutic agents such as a compound or composition described herein). In specific embodiments, the therapeutic treatment includes the amelioration of at least one measurable physical parameter of an HIV infection. In other embodiments, the therapeutic treatment includes the inhibition of the progression of an HIV infection, either physically by, e.g., stabilization of a discernible symptom, physiologically by, e.g., stabilization of a physical parameter, or both. In other embodiments, the therapeutic treatment includes the reduction or stabilization of HIV infections. Antiviral drugs can be used in the community setting to treat people who already have HIV infection to reduce the severity of symptoms and suppress the infection. Treating and HIV infection includes reducing or eliminating an HIV reservoir in a patient.

As used herein, the term "HIV reservoir" refers to a group of cells in a patient that are infected with HIV but have not produced new HIV (i.e., are in a latent stage of infection) for many months or years. Very early during acute HIV infection, a latent reservoir is established and despite effective combination anti-retroviral therapy (cART), HIV persists in latently infected cells. If a patient having a latent HIV infection stops treatment with cART, the presence of an HIV reservoir in a patient can allow an active HIV infection to become re-established in the patient.

The terms "prophylaxis", "prophylactic", "prophylactic use", and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease.

As used herein, prophylactic use includes use to prevent contagion or spread of the infection in populations or individuals at high risk of HIV infection. Prophylactic use may also include treating a person who is not ill with HIV or not considered at high risk for contracting HIV, in order to reduce the chances of becoming infected with HIV and passing it on to another person.

In some embodiments, the methods of the disclosure are applied as a prophylactic measure to members of a community or population group, specifically humans, in order to prevent the spread of infection.

As used herein, an "effective amount" refers to an amount sufficient to elicit the desired biological response. In the present disclosure the desired biological response is to inhibit the replication of HIV, to reduce the amount of HIV, or to reduce or ameliorate the severity, duration, progression, or onset of an HIV infection, prevent the advancement of an HIV infection, prevent the recurrence, development, onset or progression of a symptom associated with an HIV infection, or enhance or improve the prophylactic or therapeutic effect(s) of another therapy used against HIV infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other antiviral agents, e.g., when co-administered with an anti-HIV medication, an effective amount of the second agent will depend on the type of drug used. A safe amount is one with minimal side effects, as can readily be determined by those skilled in the art. Suitable dosages are known for approved agents and can be adjusted by the skilled artisan according to the condition of the subject, the type of condition(s) being treated and the amount of a compound described herein being used. In cases where no amount is expressly noted, a safe and effective amount should be assumed. For example, compounds described herein can be administered to a subject in a dosage range from between approximately 0.01 to 100 mg/kg body weight/day for therapeutic or prophylactic treatment.

As used herein, a "safe and effective amount" of a compound or composition described herein is an effective amount of the compound or composition which does not cause excessive or deleterious side effects in a patient.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe a safe and effective amount of the compounds described herein required to treat, to prevent, inhibit (fully or partially) or arrest the progress of the disease.

Dosages of the compounds described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), three times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc.

Preparation of Compounds Disclosed Herein

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March□s Advanced Organic Chemistry:* Reactions, Mechanisms, and Structure, 5$^{th}$ edition, John Wiley & Sons: New York, 2001 ; and Greene, T. W., Wuts, P .G. M., *Protective Groups in Organic Synthesis,* 3$^{rd}$ edition, John Wiley & Sons: New York, 1999, are useful and recognized reference textbooks of organic synthesis known to those in the art. For example, the compounds disclosed herein can be synthesized by solid phase synthesis techniques including those described in Merrifield, *J. Am. Chem. Soc.* 1963; 85:2149; Davis et al., *Biochem. Intl.* 1985; 10:394-414; Larsen et al., *J. Am. Chem. Soc.* 1993; 115: 6247; Smith et al., *J. Peptide Protein Res.* 1994; 44: 183;

ODonnell et al., *J. Am. Chem. Soc.* 1996; 118:6070; Stewart and Young, *Solid Phase Peptide Synthesis,* Freeman (1969); Finn et al., *The Proteins,* 3rd ed., vol. 2, pp. 105-253 (1976); and Erickson et al., *The Proteins,* 3rd ed., vol. 2, pp. 257-527 (1976). The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt, ester or prodrug thereof.

In general, compounds of Formula (I) can be synthesized according to Scheme 1.

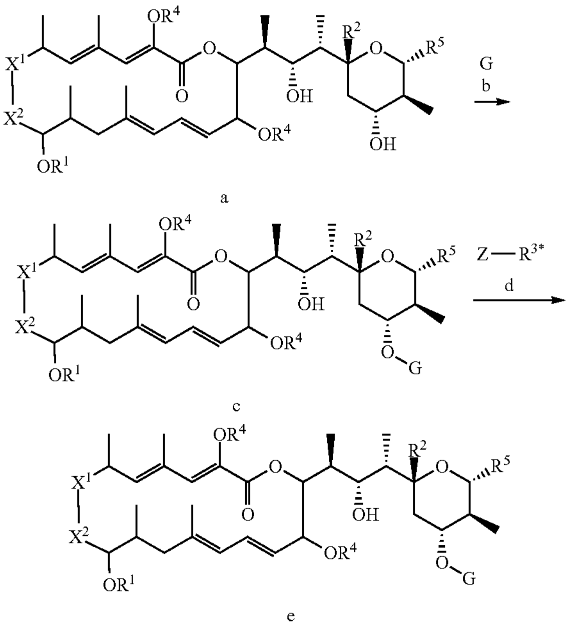

G = activating reagent
Z = reactive group

Compounds having structure e can be synthesized using the procedure shown in Scheme 1. Reaction of an optionally substituted hydroxyplecomacrolide compound a with an activating reagent b (e.g., N,N'-Disuccinimidyl carbonate) produces O-activated plecomacrolide compound having structure c (e.g., an O-succinimidyl ester). Condensation with an appropriate derivative of radical $R^3$ d, e.g., an amine such as an amino sugar, gives compounds as described herein, i.e., compounds of Formula (I) having structure e. Further derivatization can be carried out if desired under conditions known to the skilled artisan.

Compounds a, b, d, and Ring A can be purchased commercially or prepared by a variety of methods from commercially-available starting materials.

Pharmaceutically Acceptable Salts

The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds described herein or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxylic acid group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This disclosure also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that this disclosure includes mixtures/combinations of different pharmaceutically acceptable salts and also mixtures/combinations of compounds in free form and pharmaceutically acceptable salts.

Pharmaceutical Compositions

The compounds described herein can be formulated into pharmaceutical compositions that further comprise a pharmaceutically acceptable carrier, diluent, adjuvant or vehicle. In some embodiments, the present disclosure relates to a pharmaceutical composition comprising a compound described herein, and a pharmaceutically acceptable carrier, diluent, adjuvant or vehicle. In some embodiments, the present disclosure includes a pharmaceutical composition comprising a safe and effective amount of a compound described herein or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an HIV infection in a patient.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences,* Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this disclosure. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, to the pulmonary system, such as by using an inhaler, such as a metered dose inhaler (MDI), or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer S solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure.

Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer S solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as polysorbates, sorbitan esters, and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds described herein include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzalkonium chloride. Alternatively, for ophthalmic uses, the pharmaceutical compositions may be formulated in an ointment such as petrolatum.

The compounds for use in the methods described herein can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

The disclosure will be more fully understood by reference to the examples described herein which detail exemplary embodiments. These examples should not, however, be construed as limiting the scope of the disclosure. All citations throughout the disclosure are hereby expressly incorporated by reference.

EXAMPLES

Materials and Methods

Anonymized leukocytes isolated by apheresis from healthy donors was obtained from the New York Blood Center.

Nef inhibitory compounds The following compounds were used as described below; B9 (Calbiochem, MilliporeSigma, 500653), Lovastatin (MilliporeSigma, PHR1285), Baf A1 (Cayman Chemical, 11038), Baf B1 (Cayman, 14005), Baf C1 (Cayman, 19624), Baf D (Cayman, 19438), CMA (Fermentek, 80890-47-7; Cayman, 11050)

Cell Culture

All cell cultures were maintained at 37° C. in 5% $CO_2$ humidified atmosphere. Virus producer cells (293T and BOSC cells) were maintained in D10 medium [DMEM medium (Gibco) supplemented with 100 U/mL penicillin, 100 μg/mL streptomycin, 2 mM glutamine (Pen-Strep-Glutamine, Invitrogen), 10 mM HEPES (Invitrogen), 10% fetal bovine serum (Sigma, Invitrogen), and 0.022% plasmocin (Invivogen)]. All other cells were maintained in R10 medium [RPMI-1640 medium (Gibco) supplemented as D10]. Primary T cells were cultured in R10-50 [R10 plus 50 IU/mL interleukin-2 (IL-2, Fisher 202IL010)]. CEM cell lines expressing recombinant, HA-tagged MHC-I molecules were maintained in R10 supplemented with 1 mg/mL geneticin (Gibco).

Preparation of Primary $CD4^+$ T Lymphocytes and Monocyte-Derived Macrophages

Anonymized Leukocytes isolated by apheresis were obtained from the New York Blood Center, and peripheral blood mononuclear cells (PBMCs) were isolated by Ficoll-Hypaque centrifugation using SepMate tubes (Stemcell Technologies, 85450) according to manufacturer's protocol. $CD8^+$ lymphocytes were depleted with Dynabeads according to manufacturer's protocol (Invitrogen, 11147D), and the remaining cells were incubated at a density of $2\times10^6$ cells/mL in R10 medium and stimulated with 10 μg/ml phytohaemagglutinin (PHA-L, EMD/Millipore Sigma, 431784). 16-24 hours post-PHA activation, cells were cultured in R10-50. Primary $CD4^+$ T cells were infected via spinoculation or treated for other experiments 48 hours after IL-2 addition.

Primary monocyte-derived macrophages (MDMs) were isolated and cultured as previously described and used for lysosomal pH measurements 7-10 days post-isolation.

Viral Constructs and Infections (i) HIV. NL4-3-ΔGPE-GFP (ΔGPE) wild type and HXBePLAP wild type and nef mutants have been described previously. 454-Gag-GFP was constructed from a molecular clone isolated from a donor who was treated with combination ART and had undetectable plasma viral levels. Briefly, 454LTR-GFP, created as previously described, was used, in which gfp was inserted by gene synthesis in frame at position 810, which corresponded to position 19 in the gag open reading frame and created a Gag-GFP fusion protein when expressed. To reconstruct the remainder of the genome, PCR was used to generate donor derived sequence from position 4761 in pol through the XhoI site at 9255 in nef using the re-constructed near full length 454 genome as a template. The PCR product, which contained 11-15 base pair overlaps with 454LTR-GFP, was inserted using the GeneArt Seamless Cloning Enzyme Mix (Thermo Fisher). Nef mutations were introduced into ΔGPE and 454-Gag-GFP by filling in a unique Xho I site using with klenow and re-ligating.

(i) HIV: Infectious supernatants were prepared by co-transfection of 293T cells using polyethylenimine (PEI) as previously described with each viral construct, the HIV packaging plasmid pCMV-HIV, and pHCMV-G at a mass ratio of 1:1:1. 293T cells were maintained and transfected in D10 medium. Infections were performed by spinoculation at 1,050 xg for 2 hours at room temperature at a density of $1.0\times10^6$ cells/mL. Primary cells were spinoculated in undiluted infectious supernatants supplemented with 4 μg/mL hexadimethrine bromide (polybrene, Sigma-Aldrich, H9268). Cell lines were spinoculated with infectious supernatants diluted in D10 to achieve the desired MOI (approximately 50% infection) in the absence of polybrene. Following spinoculation, infectious supernatants were replaced with the appropriate culture medium for the infected cell type.

(ii) MSCV: Murine stem cell virus internal ribosome entry site GFP (pMIG) constructs containing various nef alleles were generated as previously described. Retroviral supernatants were prepared using BOSC cells transfected with the pMIG constructs, the retrovirus packaging vector pCL-Eco (65) and pHCMV-G using PEI as described above for HIV. Viral supernatants were collected 48 h post-transfection, clarified by centrifugation, stored at −80° C., and transductions were performed as described for HIV constructs.

(iii) Adenovirus: Nef-expressing and control adenoviruses were obtained from the university of Michigan Gene Vector Core (vector clone: Ad-Ef1a.dIE3 #6, Nef clone: Ad-EF1 Nef.dIE3 #2) as previously described (35). CEM-A2 cells were transduced in serum-free R10 medium for 6 hours at a concentration of $1.0\times10^6$ cells/mL, then R10 with 20% FBS was added to achieve a density of $5.0\times10^5$ cells/mL in R10.

Flow Cytometry Surface Staining

All flow cytometry stains were performed on ice in FACS buffer (2% fetal bovine serum, 1% human serum (Fisher, BP2525), 2 mM HEPES, 0.025% sodium azide (Sigma) in PBS). Briefly, cells were resuspended in primary antibody diluted in FACS buffer for 20 min., washed once in FACS buffer, resuspended in secondary antibody diluted in FACS buffer for 15 min., washed once in FACS buffer, and fixed in 2% paraformaldehyde. Primary antibodies against the following proteins were used: HLA-A2 (BB7.2 from HB-82 hybridoma as previously described, 0.5 μg/mL), Bw4 (Bw4-APC (Miltenyi, 130-103-848, 1:50), Bw6 (Bw6-APC (Miltenyi, 130-099-845, 1:50)), pan MHC (w6/32 (Fisher, MA1-70111, 1:1000), PLAP (PLAP-647 (Santa Cruz Biotechnology, clone 8B6, 1:1000), CD4 (Fisher, 555344, 1:1000), and HA (HA.11, Covance, 1:100).

Secondary antibody for BB7.2 was goat anti-mouse IgG2b-AF647 or -AF546 (Invitrogen, 1:2000), for w6/32 secondary was goat anti-mouse IgG2a-PeCy7 (Abcam, 1:1000), for CD4 the secondary utilized was goat anti-mouse IgG1-PE (Invitrogen, 1:1000), for HA.11 the secondary was goat anti-mouse IgG1-AF647 (Invitrogen, 1:1000).

2 μg/mL 7-aminoactinomycin D (7-AAD; Calbiochem) or 4 ng/mL DAPI (4',6-diamidino-2-phenylindole; Thermo Scientific) viability dyes were included with secondary antibodies in staining protocols. In all experiments, cells were gated sequentially by forward scatter vs. side scatter for cells, doublet exclusion (forward scatter area vs. height) for singlets, and exclusion of viability dye for viable cells. Flow cytometry data were collected with a BioRad Ze5 cytometer, a MoFlo Astrios cytometer, or a BD FACScan cytometer with Cytek 6-color upgrade, and all flow cytometry data were analyzed with FlowJo software.

MTT Assay $CD4^+$ T cells were plated at a density of $1\times10^5$ cells in 200 μL R10-50 in flat-bottom 96-well plates 4 days post-stimulation with PHA. Cells were exposed to titrations of plecomacrolides or solvent controls for 72 hours in culture, at which point viability was assessed relative to solvent by MTT assay in experimental duplicates. Equal volumes of cell culture medium containing $CD4^+$ T cells were pelleted in 96-well round-bottom plates and incubated in 4.5 mg/mL MTT (Fisher, M6494) in R10 with no Phenol Red at 37° C. until the purple formazan signal was clearly visible. The absorbance of cell pellets resuspended in DMSO was measured at 595 nm on a Molecular Devices Emax precision microplate reader and compared a standard curve of known viable cell numbers to ensure the experimental samples fell within the linear range of the assay.

Lysosensor Yellow/Blue Dextran Analysis of Lysosomal pH

To measure the lysosomal pH in human monocyte-derive macrophages (MDMs), MDMs adhered to 24-well plates were exposed to 500 μg/mL Lysosensor Yellow/Blue dextran, 10,000 MW (ThermoFisher, L22460) in R10 for 24 hours. MDMs were then exposed to plecomacrolides for 1 hour and harvested with 0.05% Trypsin-EDTA (Gibco 25300054). Cells were washed twice in FACS buffer, and analyzed on a MoFlo Astrios flow cytometer, with blue signal excited from a 354 nm laser and yellow signal excited from a 405 nm laser. A standard curve was generated by resuspending MDMs in equilibration buffers of known pH as previously described. The ratio of blue:yellow fluorescence intensity was calculated for each cell, the median blue:yellow ratio for the cell population for each condition was obtained, and the lysosomal pH in MDMs was calculated for each condition using the standard curve.

Lysotracker Flow Cytometry Assay

Cells were treated with plecomacrolides at a density of $1\times10^6$ cells/mL for 24 hours, then treated with 100 nM LysoTracker Red DND-99 (Fisher, L7528) in PBS at a density of $1\times10^6$ cells/mL for 1 hour at 37° C., washed twice in PBS, and fixed in 2% PFA before flow cytometric analysis on a BioRad Ze5 flow cytometer.

Confocal Immunofluorescence Microscopy

For HLA-A2 staining, sorted $PLAP^+$ $CD4^+$ T cells isolated as previously described were attached to Poly-L-lysine (Sigma Aldrich) coated chambered slides (Fisher 154534), fixed in PBS+2% PFA and permeabilized in PBS+0.2% Tween 20. Staining was performed as previously described (19) with primary antibody against HLA-A2 (BB7.2, 2 μg/mL) and secondary goat anti-mouse IgG2b-AF546 (Invitrogen, A21143, 1:250). Slides were coated with ProLong Gold Antifade Mountant, coverslips were added, and images were collected on a Leica SP5 Confocal microscope using identical instrument settings for each sample.

Western Blotting

Sorted $PLAP^+$ $CD4^+$ T cells isolated as previously described were pelleted and lysed in Blue Loading Buffer (Cell Signaling Technology, 56036S) with DTT according to manufacturer's protocol. Lysates were sonicated with a Misonix Sonicator (QSonica) at 100 amps for four minutes, boiled at 95° C. prior to loading onto Criterion Tris-HCl gels (Bio-Rad Laboratories, Hercules Calif.), and separated by gel electrophoresis. Gels were transferred onto PVDF transfer membrane (Life Technologies) for 90 minutes at 350 mA. Membranes were blocked in 5% milk (LabScientific Inc., Highlands, N.J.) in TBS-t (0.05% Tween 20, 0.15M NaCl, 0.01M Tris pH 8.0) for 1 hour. Antibodies against the following proteins were used for western blotting: clathrin adaptor protein AP-1 γ (Fisher, 610386, 1:100); Nef (2949, AIDS Research and Reference Reagent Program, Division of AIDS, National Institute of Allergy and Infectious Diseases, NIH, Ron Swanstrom, 1:500); MHC-I heavy chain (HC.10, prepared as described; CD4 (Abcam, 133616, 1:1000); HA (HA.11, Covance), glyceraldehyde-3-phosphate dehydrogenase (Abnova, 32C) and AP-1 μ1 (RY/1, Dr. Linton Traub, University of Pittsburgh). The secondary antibody for GAPDH and HA.11 was Rat anti-Mouse IgG1-horesradish peroxidase (HRP, Invitrogen). The secondary antibody used for Nef 2949, CD4, and and RY/1 was Goat anti-Rabbit IgG-HRP (Invitrogen). The secondary antibody used for AP-1 γ was Goat anti-Mouse IgG1-HRP (Zymed Laboratories Inc.). The secondary for HC.10 was Rat anti-Mouse IgG2a-HRP (Invitrogen).

Western blotting results were quantified using Photoshop by determining the average pixel density in a box of equal size over each band from a single, unedited film displaying a single gel. Background pixel density was subtracted. No quantification comparisons were made from bands on different films or gels at any point.

HLA-A2 Coimmunoprecipitation

Immunoprecipitation of CEM cell lysates with BB7.2-conjugated beads was performed as previously described. Briefly, $25\times10^6$ CEM-A2 cells were transduced with Nef-expressing or control adenovirus. 48 hours post-infection, cells were counted and resuspended at a density of $1\times10^6$ cells/mL R10 supplemented with 35 mM $NH_4Cl$, 1.25 nM CMA, or solvent control for 24 hours. Cells were pelleted, washed twice in PBS, and lysed in 1% digitonin lysis buffer (1% digitonin (Wako, 043-21371), 100 mM NaCl, 50 mM Tris, pH 7.0, 1 mM $CaCl_2$, and 1 mM $MgCl_2$) as previously described. 1% of the lysate was removed for input controls. After overnight pre-clear with isotype control antibody and protein A/G agarose (EMD Bioscience, IP-10), lysates were immunoprecipitated overnight with protein A/G agarose cross-linked to BB7.2. After pulldown, resin was washed five times in 0.1% digitonin wash buffer, and proteins were eluted by incubating in 150 mM dithiothreitol (Invitrogen) for 30 minutes at 37° C. and analyzed by western blot.

In vitro investigations of AP-1:Nef:MHC-I complexes

Recombinant Protein Expression and Purification

The His6- and GST-tagged AP-1 core, mouse AP1M1 (157-423) (referred as μ1-CTD), human Arf1 (17-181)-Q71L, human MHC-I (338-365)-NL4-3 Nef, HIV-1 NL4-3 Nef constructs and protein purification were previously described. For GST pull down assay, codon-optimized human MHC-I (338-365) was subcloned into pGST parallel2 vector using BamHI/XhoI sites, fused an N-terminal GST tag and a TEV cleavage site. PCR encoding HIV-1 Nef or SIVsmm Nef fused with GFP was subcloned into LIC 2BT vector (Macrolab), expressed as a TEV-cleavable N-terminal His6 tag and C-terminal uncleavable GFP tag.

His-NL4-3 Nef-GFP or His-SIVsmm Nef-GFP constructs were expressed in BL21 (DE3) star cells (Life technologies, Grand Island, NY), 0.3 mM IPTG induced at 25° C. overnight. The purification was carried out using Ni-NTA resin. The eluate was subjected to a HiLoad 16/60 Superdex 75 column in the buffer of 20 mM Tris pH 8, 300 mM NaCl, 0.1 mM TCEP.

His-MBP tagged μ1-CTD was expressed in BL21 (DE3) star cell and induced with 0.3 mM IPTG at 20° C. overnight. The clarified lysate was purified by Ni-NTA resin. The protein was eluted with 0.1 M imidazole in the buffer of 50 mM Tris pH 8, 300 mM NaCl, followed by TEV cleavage at 4° C. overnight. Next day, the sample was diluted 2 times by SP buffer A (30 mM Tris pH 8), and then loaded onto a HiTrap SP HP 5 ml column (GE healthcare). The elution on SP column was performed with 10 CV linear gradient from 0-1 M NaCl in SP buffer A. The sample fractions were pooled together then subjected to a 16/60 Superdex 75 column in the buffer of 20 mM Tris pH 8, 300 mM NaCl, 0.1 mM TCEP.

GST tagged MHC-I tail was expressed in BL21 (DE3) star cells by induction at 20° C. overnight. The purification was carried out using glutathione-Sepharose 4B resin, the elution was then subjected to a HiLoad 16/60 Superdex 75 column in the buffer of 20 mM Tris pH 8, 150 mM NaCl, 0.1 mM TCEP.

AP-1:Arf1: MHC-I-Nef Complex Assembly

Recombinant AP-1 core was mixed with Arf1-GTP and MHC-I-Nef at the molar ratio of 1:4:6, then incubated at 4° C. overnight. Next day, the mixture was subjected to a Superose6 10/100GL column in the buffer of 20 mM Tris pH 8.0, 150 mM NaCl, 5 mM $MgCl_2$, 0.3 mM TCEP. The early eluted peak, corresponding to AP-1 trimer assembly, was pooled together then concentrated to 25 μM. Each AP-1 trimer complex consists of three AP-1 core, three MHC-I-Nef and six Arf1-GTP molecules.

Differential Scanning Fluorimetry (DSF) Assay

DSF assays were performed using a Stratagene Mx3000P RT-PCR (Stratagene, La Jolla, CA) to monitor protein unfolding by the florescence increasing of SYPRO Orang (Invitrogen, Carlsbad, Calif.). Briefly, Sypro Orange (5000× concentration in DMSO) was first diluted to 1000× using DMSO, then diluted to 100× using the assay buffer. The final volume of the reaction was 20 μl. Protein samples with the compound NP1 (final at 6 or 12 μM) or with the DMSO control were first incubate at 4° C. for one hour, then mixed with Sypro Orange dye in the 96 Well Polypropylene Plate (Agilent Technologies, Santa Clara, Calif.). DMSO concentration in each well was fixed at 5% (v/v). Final concentrations of the proteins were 6 μM in the assay buffer of 20 mM HEPES pH 7.5, 200 mM NaCl, 1 mM TCEP, and the final dye was used at 8×. The Fluorescent intensity was measured using the SYBR green filter over the temperature range of 25 to 90° C. in 1 degree/min increments. After subtracting fluorescence from DMSO control reaction without protein, the average fluorescent intensities were plotted as a function of temperature. Measurements were repeated at three times and the data were processed using Origin software (OriginLab, Northampton, Mass.). The fluorescence intensity (before post-peak region) was fitted to Boltzmann equation to obtain melting temperature (Tm).

CTL Clones

CTL clones were isolated by limiting dilution from HIV-1- infected individuals. Clonality of the line was established by demonstration of unique T cell receptor usage. The CTL clones were maintained in culture with periodic re-stimulation as previously described except for the following changes; CTL clones were stimulated with anti-CD3 clone 12F6 (NIH AIDS Reagent Program) and cultured with IL-2 (NIH AIDS Reagent Program, Hoffman-La Roche). Peripheral blood mononuclear feeder cells were isolated from leukopaks (New York Blood Center) and X-irradiated with 30 cGy in R10 medium. Irradiations were performed using a Kimtron IC 225(Kimtron Medical) at a dose rate of approximately 2 Gy/min in the University of Michigan Comprehensive Cancer Center Experimental Irradiation Core (Ann Arbor, Mich.). CTL clones 115B15 and 161JXA14 both recognize HIV gag amino acids 77-85; SLYNTVATL presented by MHC-I HLA-A2 (71).

Flow Cytometric CTL Killing Assays

CTL elimination assays were performed as previously described with the following modifications: 72 hours post-infection primary $CD4^+$ T cells were stained with CellTracker Green (Fisher, c7025) according to manufacturer's protocol and treated with 0.5 nM CMA or solvent control for 24 hours. 50,000 target cells were used per condition, and following the 4 hours of co-culture, the cells were stained with DAPI as a viability dye in addition to anti-PLAP and BB7.2 antibodies. Viable target cells were separated by gating for cells that were CellTracker Green-positive and excluded DAPI. The proportion of $PLAP^+$ cells present in each condition was divided by that in the average of target cells-only conditions (E:T=0:1) to report the proportion of $PLAP^+$ cells surviving in the presence of CTLs. All samples were performed in experimental duplicates, except the target cells-only conditions (E:T=0:1), which were performed in quadruplicate. Flow cytometry data were collected on a Bio-Rad Ze5 cytometer.

Calculations and Statistical Analyses

Fold inhibition=Fold downmodulation HLA-$A2_{solvent}$/Fold downmodulation HLA-$A2_{sample}$ Normalized Nef activity=Fold downmodulation HLA-$A2_{Sample}$/Fold downmodulation HLA-$A2_{solvent}$.

Percent restoration=100*($MFI_{infected,\ sample}$−$MFI_{infected,\ solvent}$)/($MFI_{uninfected,\ solvent}$−$MFI_{infected,\ solvent}$), where MFI=median fluorescence intensity of MHC-I All statistical analyses were performed using GraphPad Prism software as described in the Fig. legends for each experiment. Curves were generated using GraphPad Prism software using [Inhibitor] vs. response with variable slope (four parameters), and the extra sum-of-squares F test was used to compare the $EC_{50}$ for different curves.

Example 1

Screening for Natural-Product Inhibitors of HIV Nef

To identify a Nef inhibitor capable of reversing MHC-I downmodulation in HIV-infected cells, a high-throughput flow cytometric screen was performed for compounds that increased expression of recombinant HLA-A2 in a CEM T cell line (CEM-A2) expressing Nef from a gutted adenoviral vector. HLA-A2 was chosen as a representative allele of MHC-I because H LA-A allotypes are strongly targeted by Nef for downregulation, HLA-A2 is the most abundant allele in most populations, and a high-affinity monoclonal antibody selective for HLA-A2 (BB7.2) is available. Initial screening of over 200,000 small molecules failed to identify convincing hits. Screening of over 40,000 natural product extracts identified 37 that were positive in the primary screen and negative in the counter screen. A secondary screen using CEM-A2 cells infected with a VSV-G pseudotyped single-round reporter virus derived from the HIV NL4-3 molecular clone (NL4-3-ΔGPE-EGFP, ΔGPE, FIG. 1A) confirmed that extracts from 11 strains inhibit Nef in the context of HIV infection.

Natural Product Nef Inhibitors are Plecomacrolides

Natural product metabolites with anti-Nef activity analyzed by NMR and mass spectrometry were identified as members of the bafilomycin (Baf) plecomacrolide family of natural products. Baf $A_1$ and $C_1$ purified from natural product extracts by standard fractionation procedures had near identical activity to commercial sources of these compounds. Baf A1 dramatically increased cell-surface HLA-A2 in CEM-A2 cells expressing Nef from the cytomegalovirus promoter in the context of an adenoviral delivery vector and the HIV LTR using ΔGPE. Nef-dependent HLA-A2 downmodulation was reduced by over ten-fold in CEM-A2 cells and by 18-fold in primary T cells transduced with ΔGPE (FIG. 1B).

Plecomacrolides Have Diverse Nef Inhibitory Potencies and Achieve Superior Restoration of MHC-I Than Recently Identified Nef Inhibitors B9 and Lovastatin The plecomacrolide family includes the bafilomycins (Baf), which have a characteristic 16-member ring, and the concanamycins, which have an 18-member ring. HIV-infected primary $CD4^+$ T cells were exposed to plecomacrolide family members, and it was determined that all achieved equivalent levels of Nef inhibition, but with variable potencies (FIG. 1C-D). CMA inhibited Nef at the lowest concentrations ($EC_{50}$=0.07 nM), while Baf C1 was most potent among the bafilomycins ($EC_{50}$=0.4 nM, Baf B1=1.6 nM, Baf A1=2.8 nM, Baf D=380 nM).

For comparison Nef inhibitors B9 and lovastatin were also tested. Both B9 and lovastatin have been reported to impair multiple Nef functions with the effects of lovastatin evident only at supratherapeutic concentrations. No effect of B9 on Nef-dependent MHC-I downmodulation was seen across a wide range of concentrations, including those that had been previously reported to inhibit Nef in cells. For lovastatin, little restoration of MHC-I was observed at 24 hours post-treatment, but lovastatin did partially restore MHC-I to the surface of Nef-expressing cells after 48 hours of exposure. However, restoration of MHC-I by lovastatin required 2,000-fold higher concentrations and did not achieve comparable levels when compared to CMA. To confirm that the negative results achieved with B9 were not due to receipt of the wrong compound, the purchased material was verified to ensure it matched the published structure of B9 by $^{1}H$ NMR and mass spectrometry analysis. Based on these results, it is clear that CMA is the most potent Nef inhibitor yet described.

CMA Restores MHC-I At Concentrations That Are Non-Toxic to Primary Cells

High-dose plecomacrolide treatment is toxic to cells, and questions remain over the safety and utility of plecomacrolides in clinical applications targeting V-ATPase activity. No toxicity was observed with 24-hour exposure to plecomacrolides in the above experiments. However, in agreement with published reports, marked toxicity was observed when primary cells were exposed to plecomacrolides at high concentrations for extended periods. Nevertheless, based on MTT and flow cytometric viability assays, inhibition of Nef in $CD4^{+}$ primary T cells occurred at concentrations that were non-toxic even with 72 hours of direct exposure (FIG. 1E). For CMA there was an 11-fold difference between the 50% effective and toxic concentrations ($EC_{50}$ and $TC_{50}$). This compared with 3.5-fold and 4.8-fold differences for Baf A1 and C1, respectively (FIG. 1E). Subsequent experiments in primary CD4+T cells showed that Nef activity was suppressed by 10-fold and maintained 95% viability in 24-h incubations with 0.5 nM CMA (FIG. 1E).

G0/G1 cell cycle arrest, a reported effect of plecomacrolide exposure, only occurred at concentrations well above the $EC_{50}$ for Nef inhibition. CD4+T cells treated with 0.5 nM CMA showed a 1.15-fold increase in the proportion of cells in S phase compared to the solvent control, but the corresponding decrease in cells in G2/M was not statistically significant. Without wishing to be bound by theory, given the small magnitude of these changes, it is unlikely that cell cycle arrest meaningfully contributes to toxicity in cells treated with 0.5 nM CMA. Thus, plecomacrolides, and particularly CMA, may be promising lead compounds for therapeutic Nef inhibition.

Figure 2:
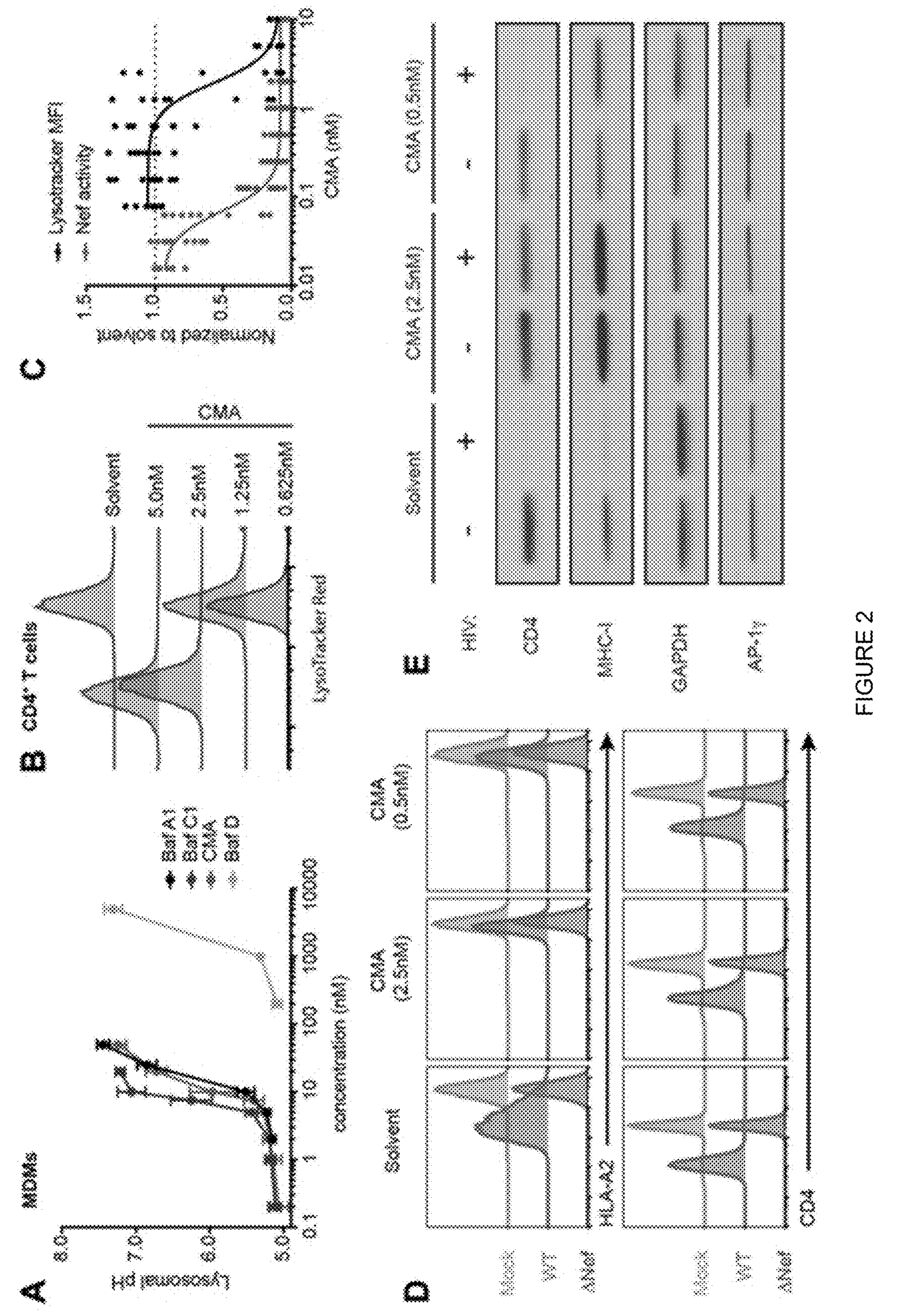
FIG. 2A is a summary graph of flow cytometric data from MDMs, treated with plecomacrolides for 1 hour as indicated (n=8 for BafA1 and BafC1,n=2 for BafD, n=6 for CMA).
FIG. 2B is representative flow cytometry histograms of primary activated $CD4^+$ T cells treated for 24 hours with CMA as indicated and incubated with Lysotracker Red for 1 hour.
FIG. 2C is a summary graph of flow cytometric data from FIG. 2B comparing the normalized median fluorescence intensity (MFI) of Lysotracker Red (black, n=9) with the normalized Nef activity from FIG. 1D (red, n=12) in $CD4^+$ T cells treated with CMA at the indicated concentrations.
FIG. 2D is representative flow cytometry histograms from primary activated $CD4^+$ T cells infected with HxBePLAP (FIG. 1 (A)) for 72 hours, sorted for $PLAP^+$ cells, and treated with CMA as indicated for 24 hours. Top histograms represent mock-infected cells, middle histograms represent sorted $PLAP^+$ cells infected with HXBePLAP (WT), and bottom histograms represent sorted $PLAP^+$ cells infected with HXBePLAP in which Nef was deleted (ΔNef, representative of 3 independent experiments).
FIG. 2E is Western blot of whole cell lysates from $CD4^+$ T cells prepared as described for FIG. 2D) (representative of 4 independent experiments).
FIG. 2F is representative confocal microscopy images of primary activated $CD4^+$ T cells prepared as described in D, stained for HLA-A2. Mock cells are uninfected. All images were captured with identical microscope settings. Solvent control is DMSO. Extra sum-of-squares F test used to compare $IC_{50}$ values of curves.
Figure 2:
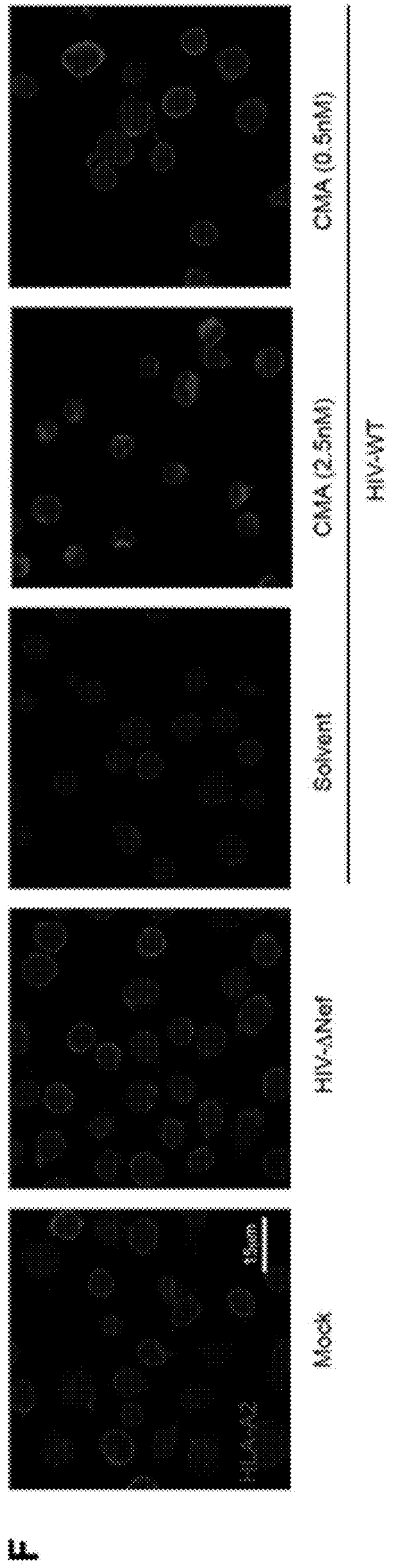

Plecomacrolides Have Distinct Nef Inhibitory and Lysosome Neutralization Potencies The toxicity associated with plecomacrolide treatment likely results from their inhibition of vacuolar $H^{+}$-ATPase (V-ATPase), which is responsible for many cellular processes, including lysosomal acidification. To determine whether inhibition of lysosomal pH might be responsible for reversal of MHC-I downmodulation in Nef-expressing cells, a previously-described method was used to measure the pH of the lysosome of primary human monocyte-derive macrophages (MDMs) by measuring ratiometric fluorescence of an endocytosed dextran. Baf A1 was first confirmed to completely neutralize lysosomal pH. Each of the plecomacrolides was then tested over a range of concentrations. Interestingly, the most potent inhibitor of Nef, CMA, was not the most potent inhibitor of V-ATPase. Instead, Baf C1 ($EC_{050}$=7.3 nM) neutralized lysosomes more potently than CMA ($EC_{050}$=12.7 nM, p<0.0001), which had comparable potency to Baf A1 ($EC_{50}$=18.5 nM, p=0.06). (FIG. 2A). This evidence indicated a qualitative separation between plecomacrolide inhibition of Nef in primary T cells and V-ATPase-mediated acidification in MDMs.

Because $CD4^{+}$ T cells did not efficiently endocytose dextran, lysosomal neutralization was assessed in these cells with Lyostracker Red dye, which freely crosses cell membranes until it reaches an acidic compartment, where it is protonated and retained. As measured by flow cytometry (FIGS. 2B-C) and confocal microscopy, the $EC_{50}$ for lysosome neutralization by CMA in primary $CD4^{+}$ T cells ($EC_{50}$=1.9 nM) was significantly higher than the $EC_{50}$ for Nef inhibition ($EC_{50}$=0.07 nM, 27-fold difference, p<0.0001). Taken together, these results indicate that CMA counteracted Nef in primary human $CD4^{+}$ T cells at concentrations that were non-toxic and did not alter lysosomal pH.

CMA Restores Cell-Surface MHC-I,But Not CD4, in Nef-Expressing Cells

Based on these data, it appeared that surface restoration of MHC-I was not simply secondary to lysosome dysregulation. To explore this hypothesis, a high dose of CMA that neutralizes the lysosome (2.5 nM) and a low dose that leaves acidic compartments intact (0.5 nM) were selected. Both MHC-I and CD4 are targeted to the lysosome by Nef, but by distinct mechanisms. MHC-I is redirected from the trans-Golgi network to the lysosome via the AP-1 adaptor complex, while CD4 is internalized from the cell surface and trafficked to the lysosome in an AP-2-dependent manner. It was found that neither dose of CMA restored CD4 to the cell surface of pure populations of Nef-expressing cells, while MHC-I was restored equally in both conditions (FIG. 2D). This indicated that CMA specifically reverses Nef-dependent MHC-I trafficking, and not all lysosome-targeted proteins, to the cell surface.

CMA Restores MHC-I In Nef-Expressing Cells With Functional Lysosomal Protein Degradation To confirm that CMA restores MHC-I by a mechanism independent of its effects on lysosomal degradation, lysosomal degradation was observed directly. As expected, both MHC-I and CD4 were degraded in Nef-expressing cells (FIG. 2E, left). A high dose of CMA, which neutralized the lysosome (FIGS. 2B-C), inhibited Nef-mediated degradation of both HLA-A2 and CD4 (FIG. 2E, center). Notably, high-dose CMA also increased MHC-I expression in uninfected cells, consistent with disruption of the steady-state turnover of MHC-I in the lysosome. Low-dose CMA, however, did not prevent degradation of CD4 and did not increase steady-state levels of MHC-I, indicating that the lysosome was functional for protein degradation. Despite this, MHC-I was not degraded in Nef-expressing cells (FIG. 2E, right). Thus, low-dose CMA treatment selectively alters the transport of MHC-I in HIV-infected primary cells, preventing redirection to the lysosome and restoring MHC-I to the cell surface.

These results were validated by immunofluorescence microscopy on pure populations of HIV-infected primary $CD4^{+}$ T cells. Cells infected with Nef-expressing HIV had a dramatic reduction in cell surface and total expression of HLA-A2 compared to uninfected cells or cells infected with Nef-deficient HIV (FIG. 2F). Exposure to 0.5 nM CMA restored the appearance of MHC-I staining to that observed in the absence of Nef (FIG. 2F). High doses (2.5 nM) of CMA caused accumulation of HLA-A2 in intracellular compartments, consistent with inhibition of lysosomal degradation. Taken together, these experiments confirmed that low doses of CMA that do not disrupt lysosomal function specifically restore MHC-I to the surface of Nef-expressing HIV-infected CD4+ T cells. These results strongly suggest a role for CMA in this process that is independent of its effects on lysosomal pH through its known target, V-ATPase.

CMA Reduces The Association of Nef and AP-1 With MHC-I

Figure 3:
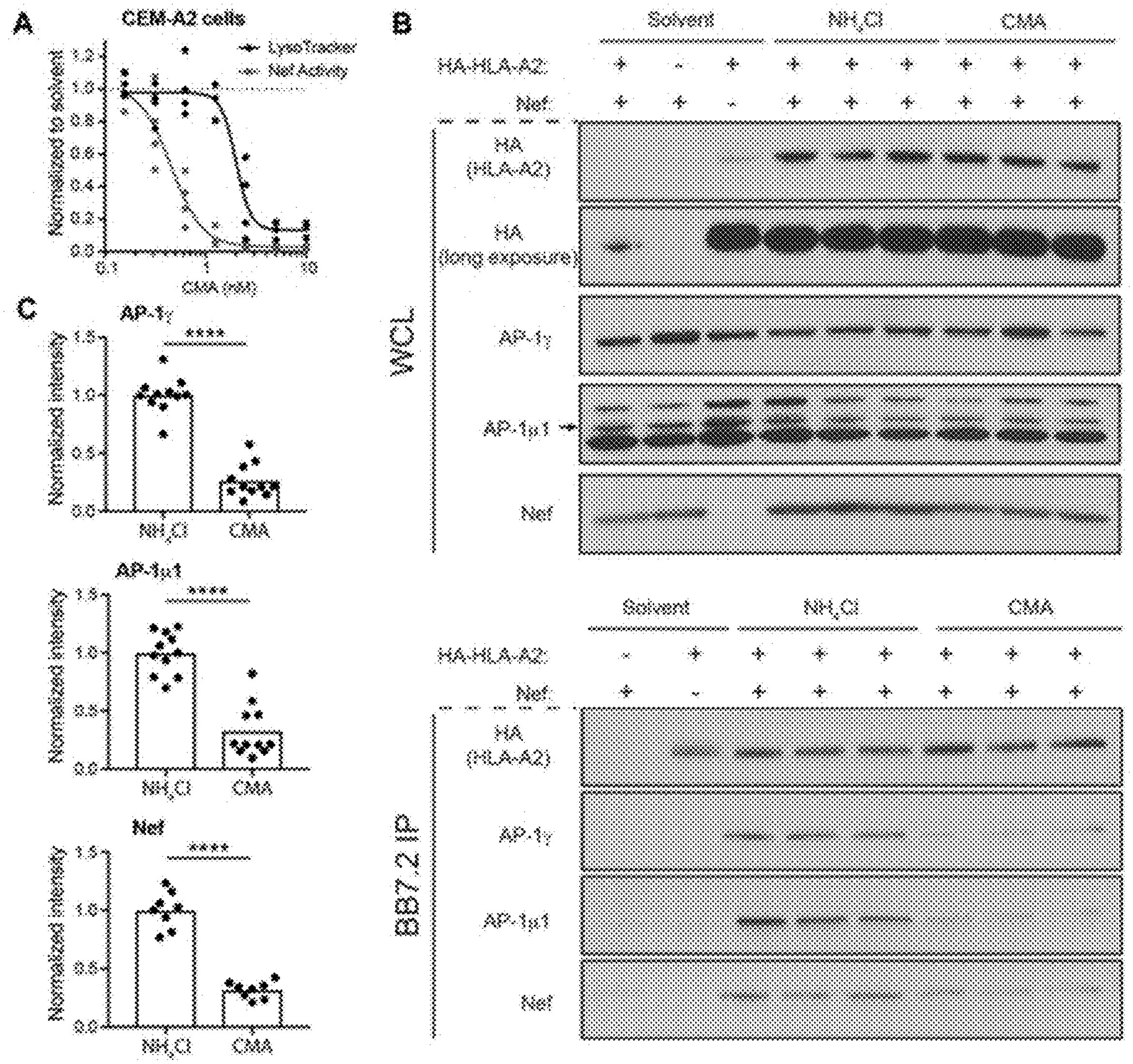
FIG. 3A is a summary graph of flow cytometric data comparing the normalized median fluorescence intensity (MFI) of Lysotracker Red (n=4) with the normalized Nef activity following ΔGPE infection (n=4) in CEM-A2 cells treated with a range of CMA concentrations.
FIG. 3B is representative Western blot depicting three experimental replicates (of 11 total replicates) of whole cell lysates before (top panel) or matched samples after (bottom panel) immunoprecipitation using BB7.2-conjugated beads (specific for HLA-A2) from CEM-SS or CEM-A2 cells infected with Nef-expressing adenovirus construct or vector control lacking Nef. $NH_4Cl$=35mM $NH_4Cl$. CMA=1.25nM CMA.
FIG. 3C is summary graphs quantifying experimental replicates of western blots for AP-1 subunits (n=11) and Nef (n=8) as in B. Band intensities were recorded for each protein from a single exposure in which all bands were visible but none were saturated. Band intensity was normalized to the intensity of HLA-A2 for each sample to account for differences in HLA-A2 recovery. Results were normalized to $NH_4Cl$, and the average of $NH_4Cl$ values was used where multiple replicates were run simultaneously as in B. ****=$p<0.0001$, unpaired two-tailed t-tests.
FIGS. 3D to 3I are differential scanning fluorimetry (DSF) plots of protein thermal stability with or without CMA treatment, showing that CMA does not affect the AP-1: MHC-I:Nef interaction in vitro. Reaction mixtures contained Sypro orange and 2-6 μM proteins in the presence or absence of 2-12 μM CMA. Sypro orange fluorescence intensity was plotted as a function of temperature for (D) μ1-CTD domain, (E) MHC-I tail fused with HIV-1 NL4-3 Nef (MHC-NL43 Nef), (F) μ1-CTD: MHC-NL43 Nef, (G) AP-1 core, (H) AP-1 trimer containing AP-1 core: Arf1-GTP: MHC-NL43 Nef, and (I) NL43 Nef alone. DMSO concentration in each reaction was fixed at 5%. Measured fluorescence intensity (before post-peak region) was fitted to Boltzmann equation to obtain melting temperature (Tm). The error bars represent the corresponding standard deviation among three replicates.
Figure 3:
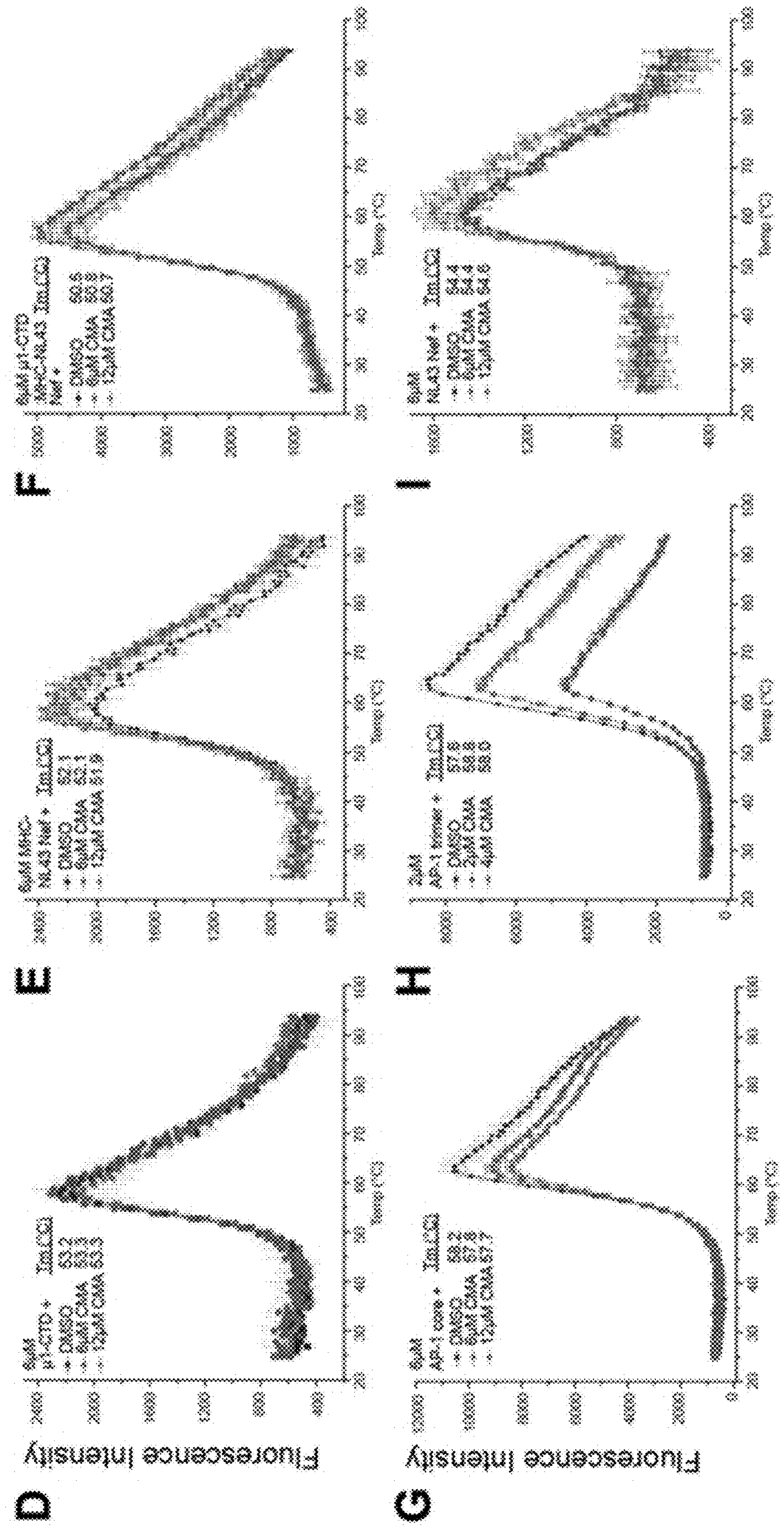

The observation that CMA selectively affects MHC-I and not CD4 degradation suggests that CMA disrupts the formation of the AP-1:Nef:MHC-I complex. To test this directly, CEM-A2 cells transduced with an adenoviral vector expressing Nef were used. This system has been used to study the formation of the AP-1:Nef:MHC-I complex under conditions where ammonium chloride prevents lysosomal degradation. Higher concentrations of CMA were required for reversal of Nef activity in CEM cells. However, 1.25 nM CMA was identified as a concentration that inhibited Nef without significantly altering intracellular acidification (FIG. 3A). This is functionally similar to 0.5 nM CMA treatment in $CD4^+$ T cells.

Because both ammonium chloride and CMA stabilized HLA-A2 expression to similar levels, a comparison between whether CMA specifically resulted in a reduction in the abundance of the AP-1:Nef:MHC-I relative to what is observed under conditions of lysosomal neutralization was made. It was found that CMA treatment led to a reproducible reduction in the abundance of Nef, AP-1μ, and AP-1μ1 subunits associating with HLA-A2 compared to cells treated with $NH_4Cl$ (FIG. 3B). These effects were highly significant when compiled across multiple experiments (FIG. 3C, $p<0.0001$). Control experiments confirmed the specificity of the assay, as detection of AP-1μ, and AP-1μ1 in pulldowns required both HLA-A2 and Nef (FIG. 3B, leftmost lanes). In addition, it was confirmed that the complex could not reliably be observed in the absence of ammonium chloride due to robust HLA-A2 degradation and minimal HLA-A2 recovery in the presence of Nef (FIG. 3B, leftmost lanes).

To determine whether CMA directly binds to components of the AP-1:Nef:MHC-I complex, differential scanning fluorimetry thermal stability assays were performed using a comprehensive panel of purified components of the Nef-MHC-I-HLA-A2 complex including the AP-1 μ1-C-terminal domain (μ1-CTD, FIG. 3D), the MHC-I tail fused with HIV-1 NL4-3 Nef (MHC-NL43 Nef, FIG. 3E), the μ1-CTD: MHC-NL43 Nef complex (FIG. 3F), the AP-1 core (FIG. 3G), the AP-1 trimer containing AP-1 core:Arf1-GTP: MHC-NL43 Nef complex (FIG. 3H), and NL43 Net alone (FIG. 3I). No significant changes in $T_m$ were observed with 1-hour incubation of any of the samples with CMA compared to solvent control, indicating that CMA does not bind directly to any of these members of the ARF-1:AP-1:Nef: MHC-I complex in vitro. Furthermore, when GST-tagged MHC-I cytoplasmic tail was immobilized on resin, the presence of CMA did not alter pulldown of NL4-3 Net, SIV Nef, or the AP-1 μ1-CTD. In summary, these results demonstrate that CMA impairs the formation of the AP-1:Nef: MHC-I complex in cells. However, this is unlikely to result from direct binding of CMA to known protein components of the complex and implicates the existence an alternative target necessary for Nef-specific MHC-I trafficking.

CMA Enhances CTL-Mediated Clearance of HIV-Infected Cells Comparably to Genetic Deletion of nef There is a large body of literature indicating that increases in cell-surface MHC-I on target cells yield proportional increases in CTL-mediated clearance of target cells. Given that Nef-expressing $CD4^+$ T cells treated with 0.5 nM CMA have near normal surface expression of HLA-A2 (FIG. 2D), it was hypothesized that CMA would eliminate Nef-mediated protection of HIV-infected cells from HIV-specific CTLs. To test this directly, in vitro flow cytometric CTL killing assays were performed with two HLA-A2-restricted CTL clones expressing T cell receptors specific for HLA-A2 presenting the Gag SL9 epitope, which is expressed in the HIV molecular clone HXBePLAP (FIG. 1A).

Figure 4:
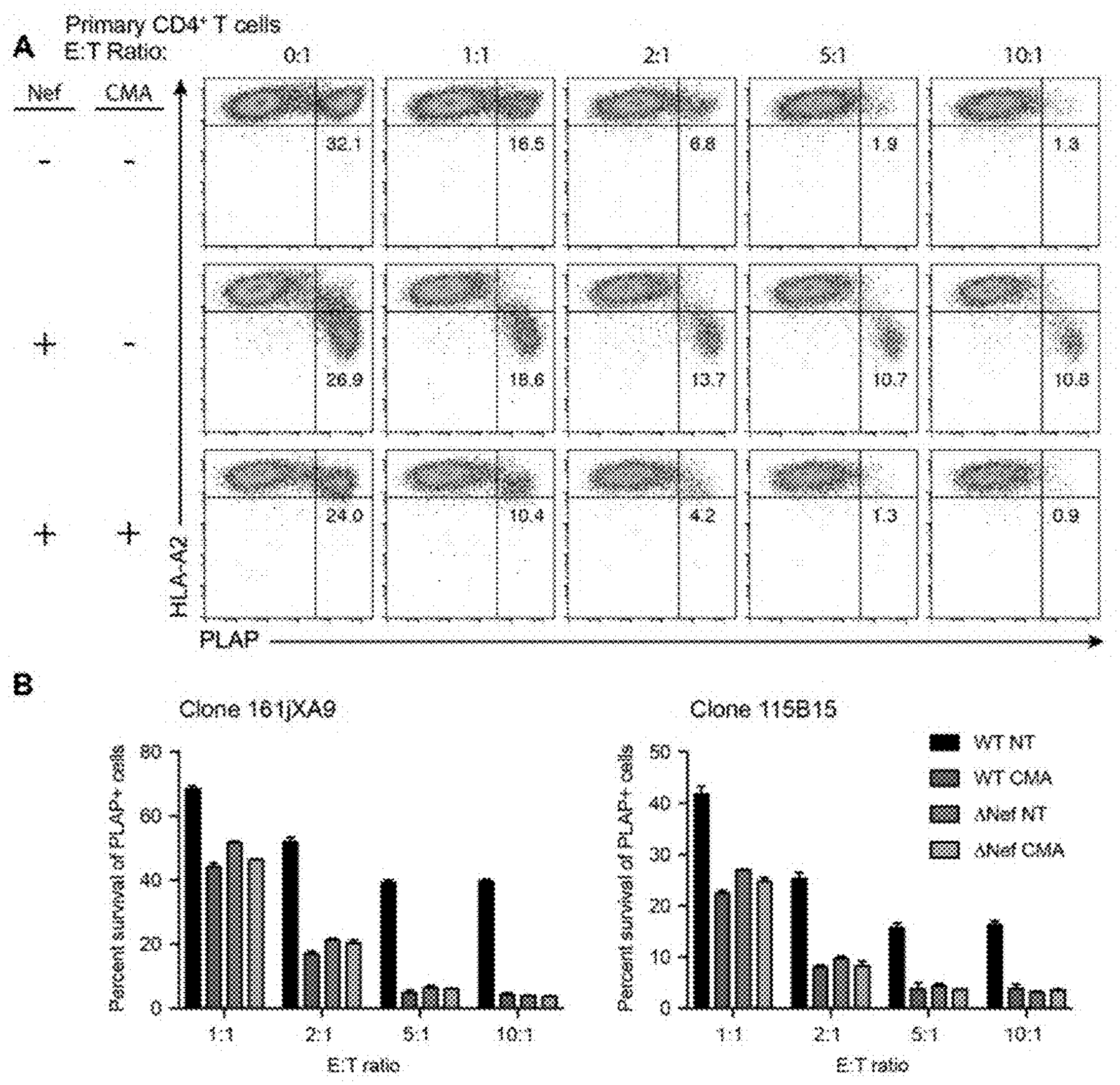
FIG. 4A is representative flow cytometry plots depicting CTL-mediated killing of CD4+ T cells infected with HXBePLAP plus or minus Nef (FIG. 1 (A)) for 72 hours and treated for 24 hours with 0.5 nM CMA or matched DMSO solvent control as indicated. Cells were gated for CD4+ T cell targets.
FIG. 4B is summary graph of results from FIG. 4A in two independent experiments using two distinct CTL clones. Each condition was performed in duplicate, and survival of $PLAP^{+}$ cells was determined by normalizing to the mean of quadruplicate 0:1 samples. Error bars represent standard deviation. WT, HXBePLAP wild-type; ΔNef, HXBePLAP in which Nef was deleted; E:T, effector:target ratio, indicates the number of anti-HIV CTLs present in the 4-hour co-culture per $CD4^{+}$ T cell target cell.

As previously observed, $PLAP^+$ cells infected with a Nef-deleted virus were efficiently eliminated by CTLs (FIG. 4A, top row). In contrast, CTL-mediated clearance of cells infected with a Nef-competent virus was notably reduced at every effector:target (E:T) ratio. Importantly, there was no further elimination of $PLAP^+$ cells when the E:T ratio was increased from 5:1 to 10:1, indicating that there was a residual population of Nef-expressing cells that were highly resistant to clearance even by a large excess of potent HIV-specific CTLs (FIG. 4A, middle row). Cells infected with Nef-competent virus and treated with 0.5 nM CMA, however, had restored HLA-A2 expression, and the $PLAP^+$ subset was efficiently eliminated by CTLs (FIG. 4A, bottom row). The effect of CMA on CTL killing of HIV-infected cells was indistinguishable from genetic deletion of Nef and was Nef-dependent, as there was no increase in clearance of cells infected with Nef-deleted virus (FIG. 4B). Importantly, when target cells from a donor lacking HLA-A2 were co-cultured with CTLs, there was no reduction in $PLAP^+$ target cells regardless of whether they were treated with CMA, validating the specificity of the CTLs and demonstrating that CMA only enhances clearance of HIV-infected cells in the presence of both Nef and specific anti-HIV CTL responses. These observations strongly confirm that low-dose CMA treatment of Nef-expressing cells restores HLA-A2 that is properly loaded with an HIV-derived peptide that can be successfully presented to CTLs without impairing responsiveness to CTL-derived lytic signals.

Previous reports have indicated that concentrations of CMA greater than 1 nM could inhibit the effector functions of CTLs, but no such effect was observed at 0.5 nM CMA. These results were confirmed using anti-HIV CTLs. No change in the clearance of SL9 peptide-pulsed target cells in the presence of 0.5 nM CMA was observed.

Figure 7:
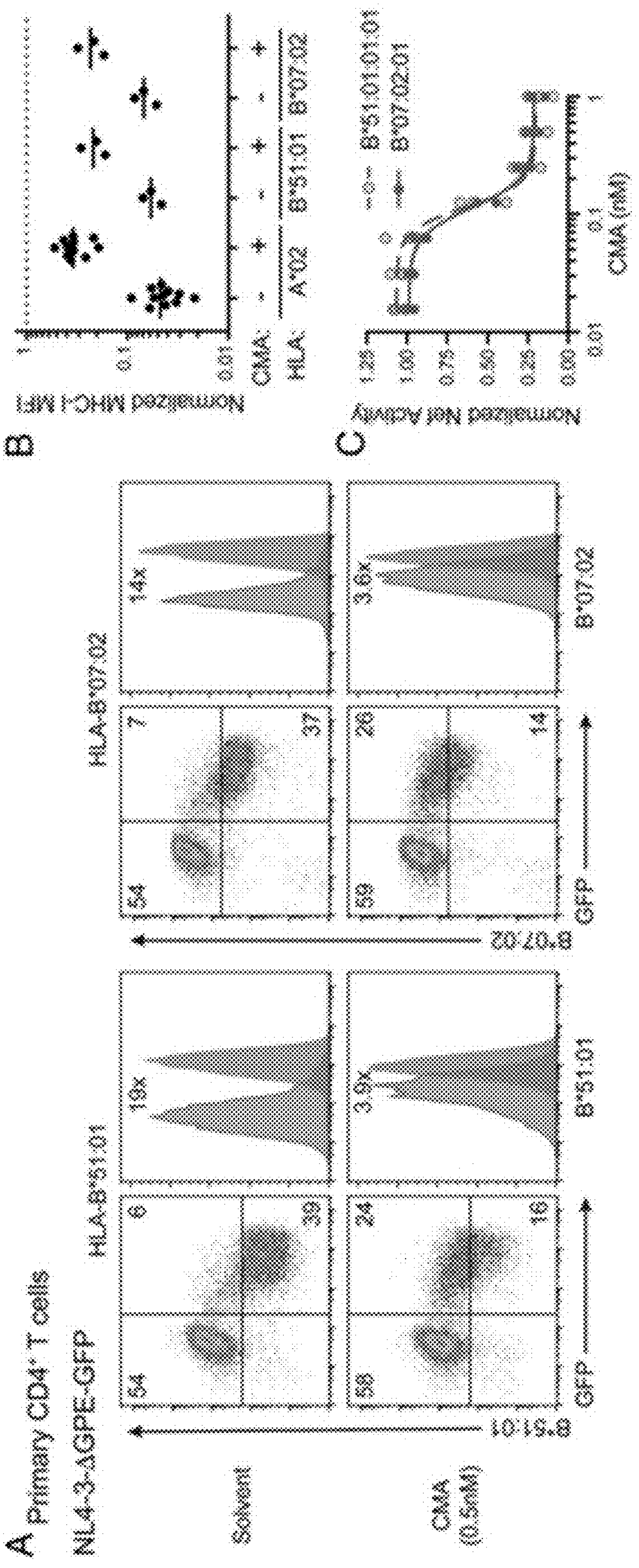
FIG. 7A is representative flow cytometry plots (n=3 independent replicates from a single donor) from primary $CD4^{+}$ T cells infected with NL4-3-ΔGPE for 48 h, treated with 0.5 nM CMA for 24 h, and stained with monoclonal antibodies to Bw4 (B*51:01) and Bw6 (B*07:02). Right side histograms are from GFP− cells; red histograms are from infected GFP+ cells.
FIG. 7B is a summary graph of data from A plotting the MHC-I MFI from infected GFP+ cells normalized to that in uninfected cells treated with solvent control (dotted line). Data for HLA-A*02 are from independent experiments with 11 different donors, data for HLA-B*51:01 and HLAB*07:02 are from three independent experiments with a single donor.
FIG. 7C is a summary graph of data from A depicting the relative Nef activity against the indicated HLA-B allotypes in cells treated with a range of CMA concentrations (n=3).
FIG. 7D is flow cytometry plots from CD4+ T cells infected with 454-Gag-GFP (FIG. 1A) and treated and stained as in A (n=1 for HLA-B allotypes, n=3 for HLA-A*02). Solvent control is DMSO. Numbers indicate the proportion of live cells in each quadrant gate or the fold change in MHC-I MFI between infected and uninfected cells.
Figure 7:
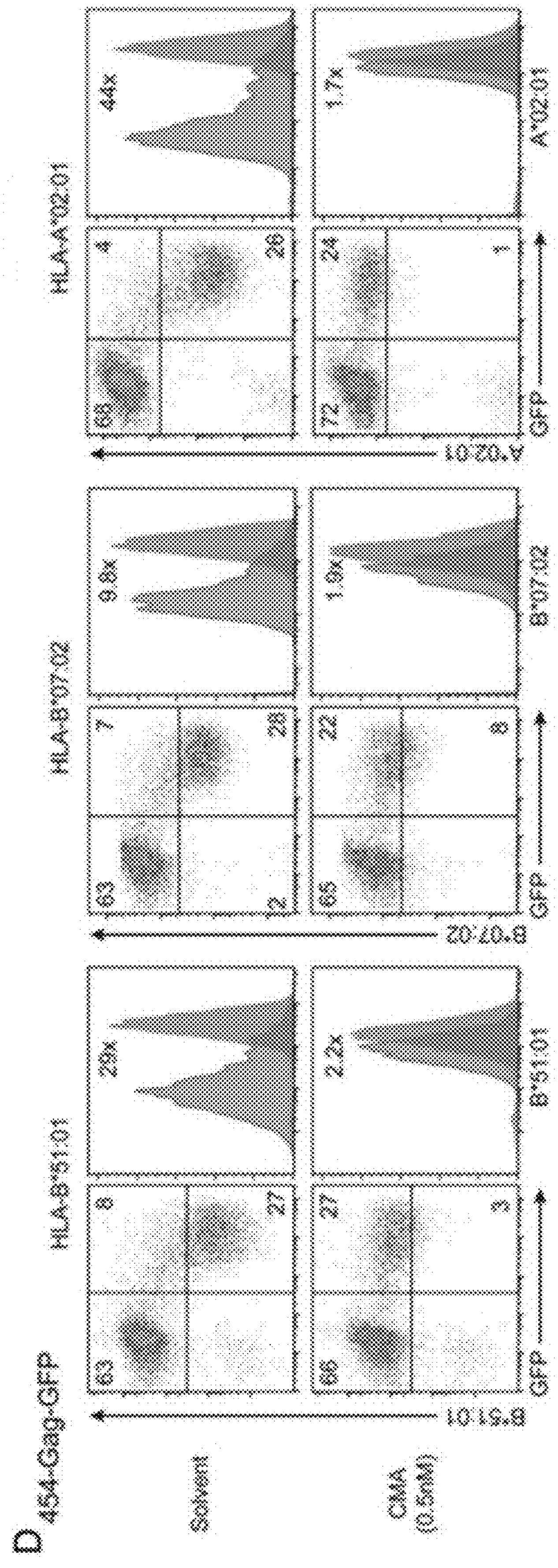

CMA Reverses Nef-Mediated Downmodulation of Diverse Forms of MHC-I in Primary Cells While Nef downregulates HLA-A allotypes with greater magnitude, HLA-B allotypes are also downregulated, and many patients possess robust HLA-B-restricted, HIV-specific CTLs. Thus, a determination was made about whether CMA would restore HLA-B expression in HIV-infected cells. Sequence differences in HLA-B allotypes classify them as either HLA-Bw4 or HLA-Bw6 serotypes. Each serotype can be detected with monoclonal antibodies, but these antibodies are cross-reactive with some HLA-A (Bw4) and HLA-C (Bw6) allotypes. A donor has been identified that was heterozygous for Bw4 (B*51:01) and Bw6 (B*07: 02) with no cross-reactive H LA-A alleles and minimal cross-reactivity from HLA-C, allowing the reliable measurement of expression of two HLA-B alleles. There was significant downmodulation of both HLA-B*51:01 and HLA-B*07:02 in cells infected with ΔGPE, which was consistently counteracted by CMA (FIG. 7A-C). The effects of Nef and CMA on both HLA-B alleles in this donor were similar in magnitude to those observed for HLA-A*02 in an array of donors (FIG. 7B). Thus, CMA can potently counteract Nef-mediated down-regulation of both HLA-A and HLA-B allotypes in primary CD4+ T cells.

Figure 5:
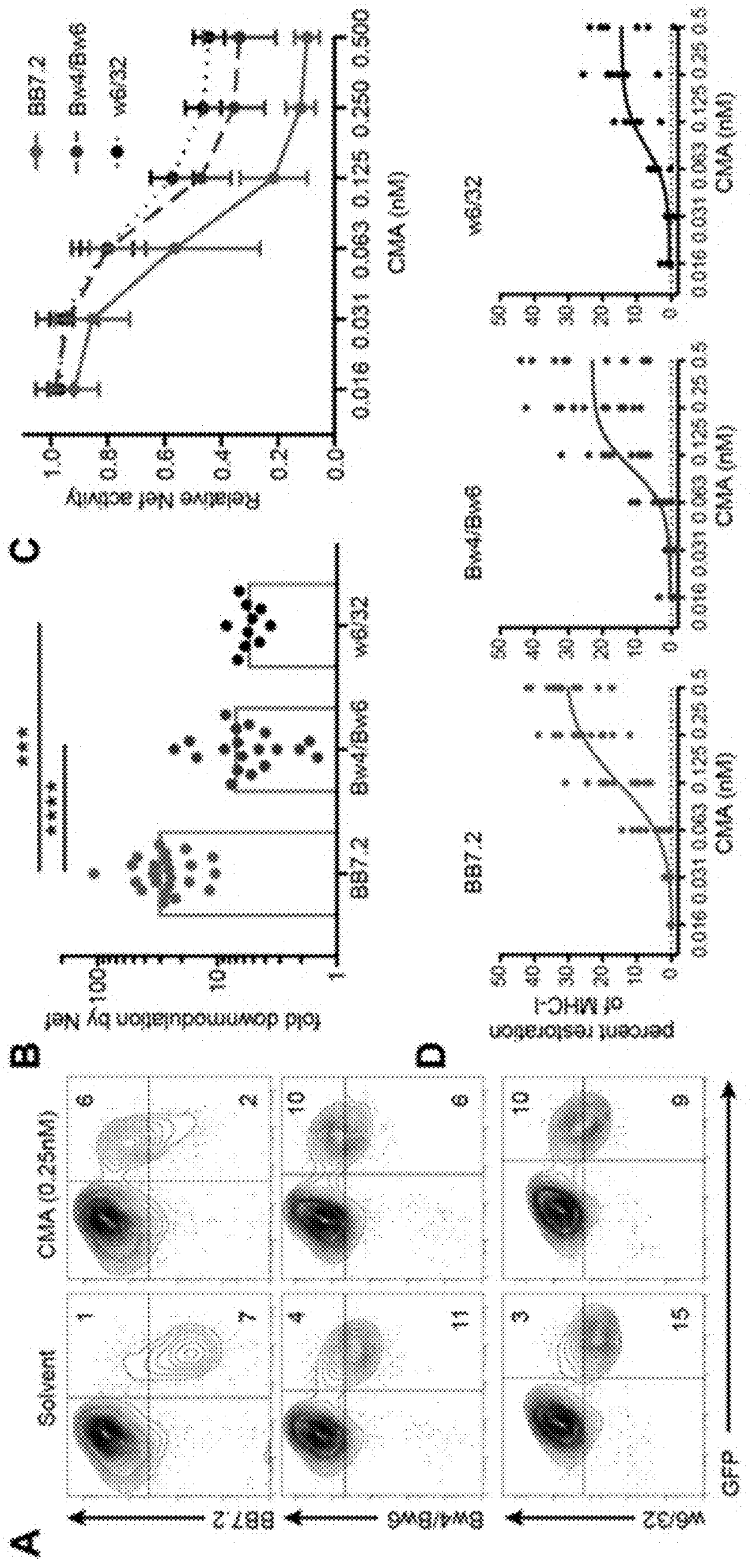
FIG. 5A is representative flow cytometry plots depicting Nef activity in $CD4^{+}$ T cells infected with NL4-3-ΔGPE for 48 hours and treated with 0.25 nM CMA for 24 hours and stained with the indicated monoclonal antibodies. BB7.2 recognizes HLA-A2; pooled antibodies directed against the Bw4 and Bw6 recognize all HLA-B allotypes plus a limited number of HLA-A and HLA-C allotypes; w6/32 recognizes all HLA allotypes. Plots were selected from the donor with fold downmodulation by Nef and percent restoration by CMA closest to median from all donors tested.
FIG. 5B is summary graph of data from FIG. 5A calculating the fold downmodulation of the indicated forms of MHC-I by Nef (n=23 for BB7.2, n=19 for Bw4/Bw6, n=10 for w6/32). **=$p<0.0001$, *=$p<0.001$, unpaired t-test.
FIG. 5C is a summary graph depicting the relative Nef activity.
FIG. 5D is a summary graph showing the percent restoration of MHC-I in $CD4^{+}$ T cells as in A treated with a range of CMA concentrations. Error bars indicate standard deviation.
FIG. 5E are flow cytometry plots from $CD4^{+}$ T cells infected with ΔGPE and 454Gag-GFP (FIG. 1 (A)) for 48 hours and treated with 0.25 nM CMA for 24 hours. Staining with BB7.2 and antibodies against the Bw4/Bw6 epitopes were performed as in FIG. 5A.
Figure 5:
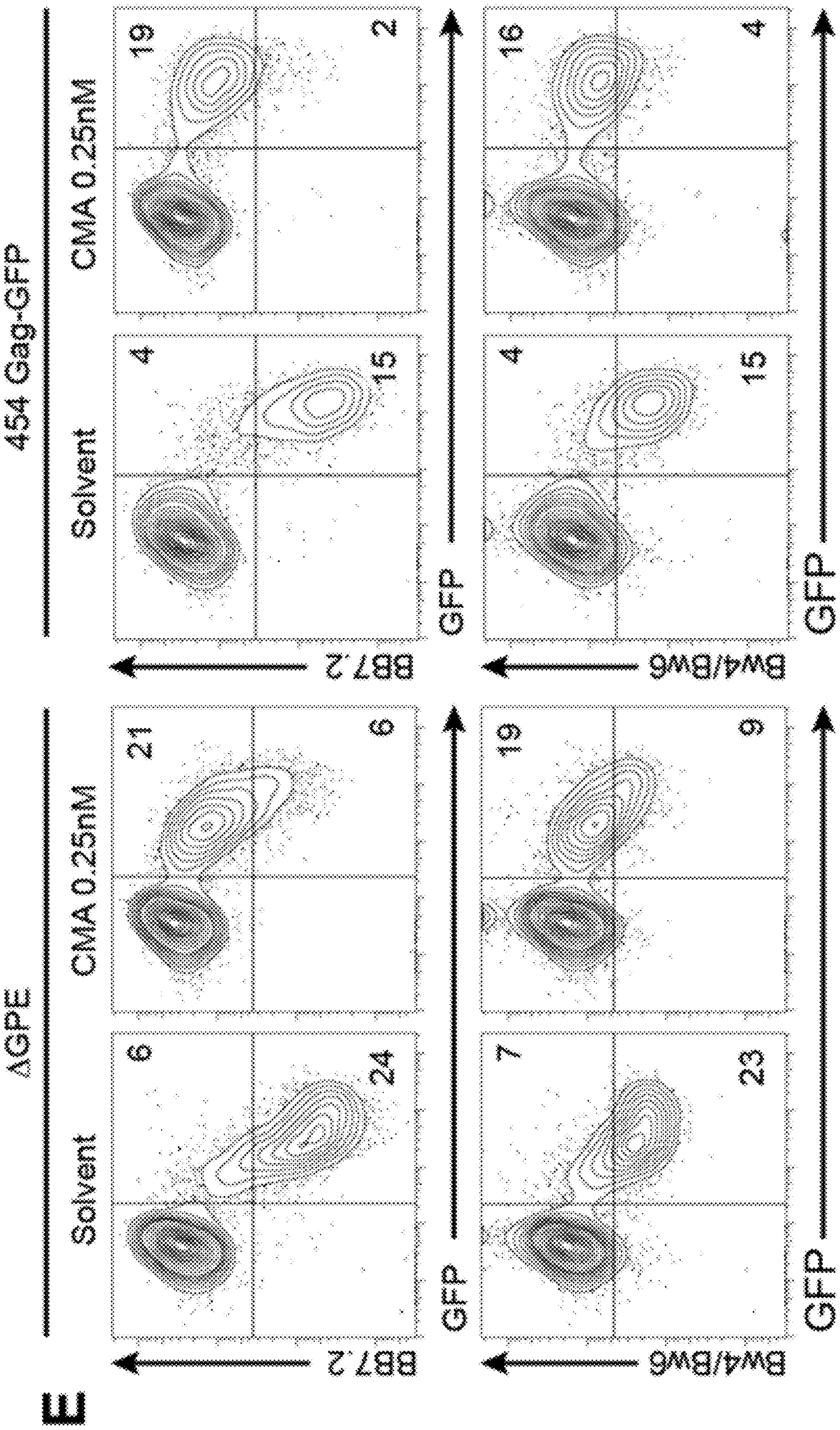

To further examine this, primary cells prepared and infected as in FIG. 1D were stained with a mixture of monoclonal antibodies collectively recognizing Bw4 and Bw6 epitopes to detect all HLA-B expression, along with possible signal from cross-reactive HLA-A and HLA-C alleles. Cells were also stained with monoclonal antibody w6/32, which recognizes most forms of MHC-I (pan-HLA), including those that are not targeted by Nef (FIG. 5A). Similar to what has previously been reported, significant downmodulation of MHC-I was observed as measured by both anti-Bw4/Bw6 staining (mean=7.3-fold, $p<0.0001$) and w6/32 staining (mean=5.7-fold, $p<0.001$) across donors. In agreement with previous reports, the degree of downmodulation was less than observed here with BB7.2 (mean=31-fold) (FIG. 5B). Nevertheless, CMA inhibited Nef down-regulation of BB7.2, Bw4/Bw6 and w6/32 staining over a similar range of concentrations (FIG. 5C and D).

A Primary HIV Isolate From An Optimally-Treated Patient Downregulates MHC-I and is Inhibited by CMA An important clinical application for Nef inhibitors that restore cellular adaptive immunity to HIV will be in the clearance of the latent reservoirs of virus that persist in optimally-treated patients, likely following therapeutic reactivation from latency. A full-length provirus was previously isolated that was expressed as residual plasma virus in an optimally-treated patient and was further shown to be infectious. Gag-Pol was deleted, and introduced was GFP, allowing identification of infected cells in a single round infection while preserving Nef from the original isolate (454Gag-GFP, FIG. 1A). $CD4^+$ T cells infected with 454Gag-GFP alongside ΔGPE demonstrated comparable downregulation of both BB7.2 and Bw4/Bw6 staining. Remarkably, CMA dramatically restored expression of both forms of MHC-I in the context of infection with the primary isolate virus (FIG. 5E). Thus, sub-nanomolar concentrations of CMA can potently restore MHC-I to the surface of primary cells expressing Nef from a primary isolate of virus from an optimally-treated patient.

Figure 6:
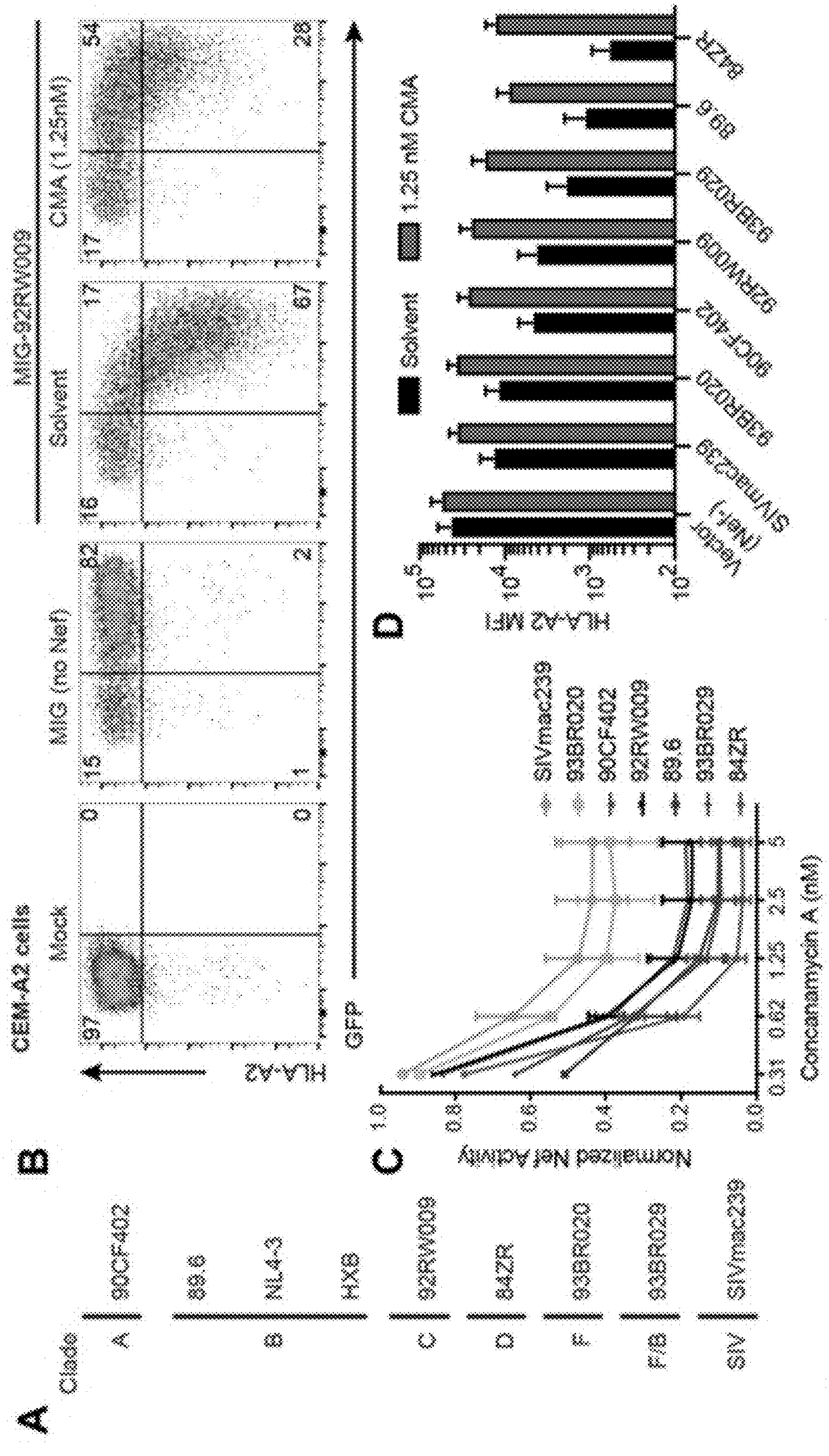
FIG. 6A is a summary of Nef alleles tested and clade of HIV or SIV to which the isolate belongs.
FIG. 6B is representative flow cytometry plots depicting CEM-A2 cells infected with MSCV-IRES-GFP (MIG) alone or expressing the Nef allele from clade C HIV isolate 92RW009, the median Nef allele from C, and treated for 24 hours with 1.25 nM CMA.
FIG. 6C is a summary graph of data from FIG. 6B, showing the relative Nef activity of each Nef allele after treatment with varying concentrations of CMA (n=3).
FIG. 6D is a summary graph of HLA-A2 MFI from experiments show in FIGS. 6B and C.
FIG. 6E to 6H are summary of flow cytometric data where CEM cells expressing the indicated HA-tagged MHC-I alleles treated as in FIG. 6D. Cell surface MHC-I expression was assessed by staining for HA, and the median fluorescence intensity in $GFP^{+}$ cells was normalized to vector control for each cell line.
Figure 6:
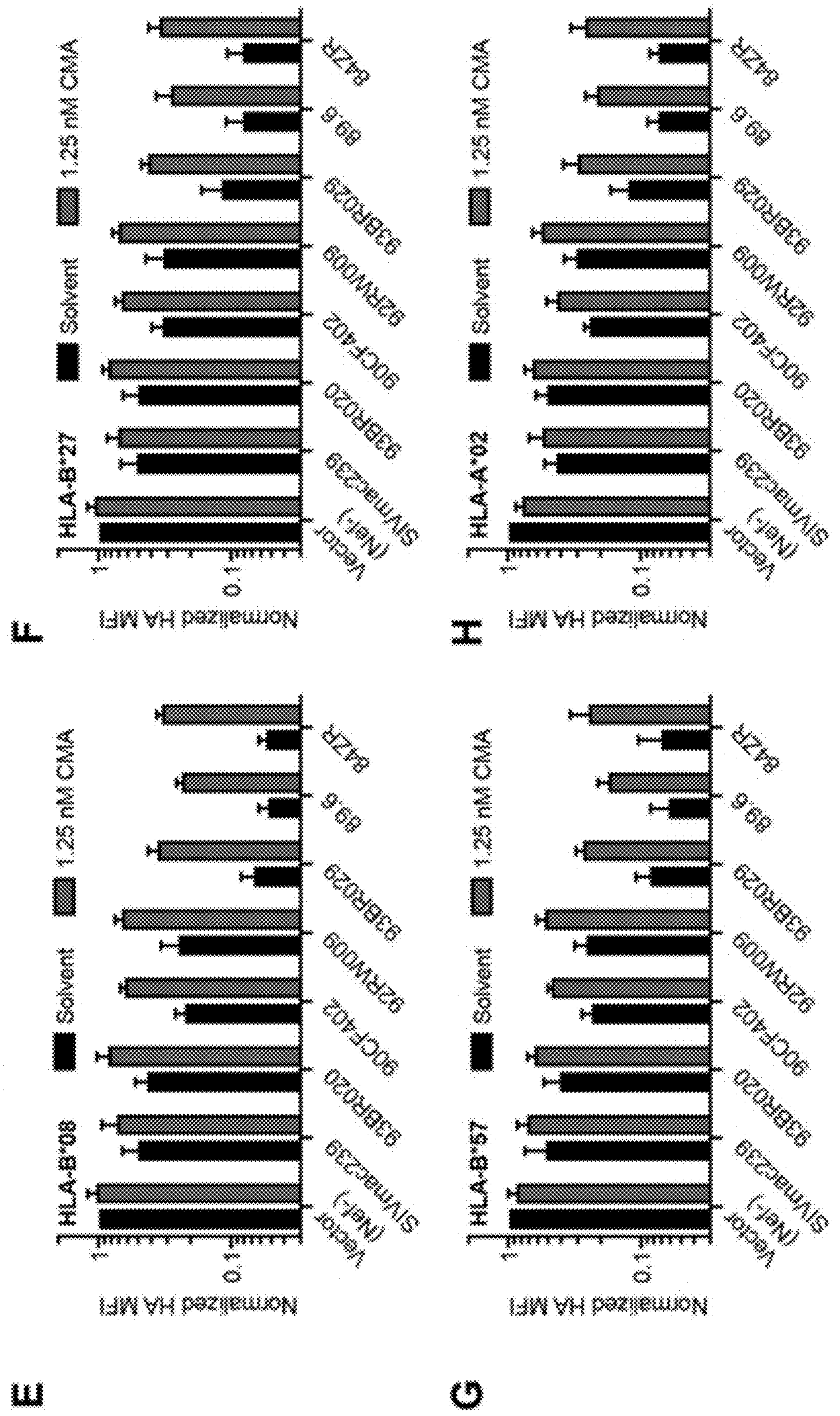

CMA Broadly Inhibits Nef Alleles From Diverse Clades of HIV and SIV Targeting a Range of MHC-I Alleles Globally, HIV possesses remarkable genetic diversity. To this point, only the inhibitory activity of plecomacrolides against Nef alleles from NL4-3, HXB and the 454 patient molecular clones, all of which are clade B viruses, had been investigated. To determine whether plecomacrolides offer broad therapeutic promise against a diverse range of Nef sequences nef alleles from HIV clades A, B, C, D, F, and F/B were tested, as well as one from simian immunodeficiency virus (SIV) (FIG. 6A) cloned into the MSCV-IRES-GFP vector (FIG. 1A). It was observed that CMA restored expression of HLA-A2 in cells expressing each nef allele, indicating that plecomacrolides broadly inhibit nef alleles from genetically diverse HIV isolates (FIG. 6C-D, red bars), and the potency of CMA was comparable for each allele (FIG. 6C). CMA was able to restore HLA-A2 expression more completely for nef alleles that downregulate HLA-A2 to a lesser extent, but had the most dramatic effect on HLA-A2 expression in cells expressing the most potent nef alleles (FIG. 6D). Similarly, CMA restored surface expression of HA-tagged MHC-I allotypes HLA-A*02, HLA-B*08, HLA-B*27, and HLA-B*57 expressed in CEM cells. Each allele of Nef downregulated each allele of MHC-I, with varying magnitudes, and CMA restored MHC-I surface expression in every context (FIG. 6E-H). These observations support the hypothesis that CMA can enhance cellular adaptive immunity regardless of the initial degree of impairment, and that CMA is likely to have broad therapeutic promise despite MHC-I polymorphisms and the global diversity of HIV.

Examples

Nef Inhibitory Compounds. The following compounds were used as described below: B9, lovastatin, Baf A1, Baf B1, Baf C1, Baf D, and CMA (concanamycin A).

Preparation of Primary CD4+ T Lymphocytes and MDMs. Anonymized leukocytes isolated by apheresis were obtained, and peripheral blood mononuclear cells (PBMCs) were isolated by centrifugation using a standard protocol. CD8+ lymphocytes were depleted with Dynabeads according to the manufacturer's protocol, and the remaining cells were incubated ata density of 2×106 cells per milliliter in R10 medium and stimulated with 10 μg/mL phytohemagglutinin (PHA). Then, 16 to 24 h post-PHA activation, cells were cultured in R10-50. Primary CD4+ T cells were infected via spinoculation or treated for other experiments 48 h after IL-2 addition. Genotyping of donor PBMCs was performed vai a standard protocol.

Primary MDMs were isolated with a CD14-positive isolation kit, stimulated with 50 ng/mL each of M-CSF and GM-CSF, and cultured via a standard protocol. MDMs were used for lysosomal pH measurements 7 to 10 days post isolation.

Viral Constructs and Infections. Infectious supernatants for HIV constructs were prepared by cotransfection of 293T cells using polyethylenimine (PEI) with each viral construct, the HIV packaging plasmid pCMV-HIV, and pHCMV-G ata mass ratio of 1:1:1. Infections were performed by spinoculation. Murine stem cell virus internal ribosome entry site GFP (pMIG) constructs containing various nef alleles were generated. Nef-expressing and control adenoviral vectors were obtained from the University of Michigan Gene Vector Core.

Flow Cytometry Surface Staining. In all experiments, cells were gated sequentially by forward scatter vs. side scatter for cells, doublet exclusion (forward scatter area vs. height) for singlets, and exclusion of viability dye for viable cells.

Lysosensor Yellow/Blue Dextran Analysis of Lysosomal pH. To measure the lysosomal pH in human MDMs, MDMs adhered to 24-well plates were exposed to 500 μg/mL Lysosensor Yellow/Blue dextran, 10,000 molecular weight (MVV) in R10 for 24 h. MDMs were then exposed to plecomacrolides for 1 h and harvested with 0.05% Trypsin-(ethylenedinitrilo)tetraacetic acid (EDTA). Cells were washed twice in FACS buffer, and analyzed on a flow cytometer, with blue signal excited from a 354-nm laser and yellow signal excited from a 405-nm laser. A standard curve was generated by resuspending MDMs in equilibration buffers of known pH. The ratio of blue:yellow fluorescence intensity was calculated for each cell, the median blue: yellow ratio for the cell population for each condition was obtained, and the lysosomal pH in MDMs was calculated for each condition using the standard curve.

Lysotracker Flow Cytometry Assay. Cells were treated with plecomacrolides at a density of 1×106 cells per milliliter for 24 h, and then treated with 100 nM LysoTracker Red DND-99 in phosphate-buffered saline (PBS) at a density of 1×106 cells per milliliter for 1 h at 37° C., washed twice in PBS, and fixed in 2% paraformaldehyde (PFA) before flow cytometric analysis on a flow cytometer.

Western Blotting. Briefly, sorted PLAP+ CD4+ T cells were isolated, pelleted and lysed, sonicated, separated by gel electrophoresis, and transferred onto a polyvinylidene difluoride (PVDF) membrane. Membranes were blocked in 5% milk prior to probing with target-specific antibodies. Western blotting results were quantified by determining the mean pixel density in a box of equal size over each band from a single, unedited film displaying a single gel. Background pixel density was subtracted. No quantification comparisons were made from bands on different films or gels at any point.

Confocal Immunofluorescence Microscopy. For HLA-A2 staining, sorted PLAP+ primary CD4+ T cells isolated as previously described (73) were attached to poly-L-lysine coated chambered slides, fixed in PBS plus 2% PFA and permeabilized in PBS plus 0.2% Tween 20. Staining was performed with primary antibody against HLA-A2 (BB7.2, 2 μg/mL) and secondary goat anti-mouse IgG2b-AF546. Slides were coated with ProLong Gold Antifade Mountant, coverslips were added, and images were collected on a confocal microscope using identical instrument settings for each sample.

HLA-A2 Coimmunoprecipitation. Immunoprecipitation (IP) of CEM cell lysates with BB7.2-conjugated beads was performed. Briefly, 25×106 CEM-A2 cells were transduced with Nef-expressing or control adenoviral vectors. Then, 48 h post infection, cells were counted and resuspended at a density of 1×106 cells per milliliter R10 supplemented with 35 mM NH4Cl, 1.25 nM CMA, or solvent control for 24 h. Cells were pelleted, washed twice in PBS, and lysed in 1% digitonin lysis buffer (1% digitonin, 100 mM NaCl, 50 mM Tris, pH 7.0, 1 mM CaCl2, and 1 mM MgCl2). Then, 1% of the lysate was removed for input controls. After overnight preclear with isotype control antibody and protein A/G agarose, lysates were immunoprecipitated overnight with protein A/G agarose cross-linked to BB7.2. After pulldown, resin was washed five times in 0.1% digitonin wash buffer, and proteins were eluted by incubating in 150 mM dithiothreitol (DTT) for 30 min at 37° C. and analyzed by Western blot.

Flow Cytometric CTL Killing Assays. CTL elimination assays were performed via a standard protocol with the following modifications: 72 h post infection, primary CD4+ T cells (target cells) were stained with CellTracker Green CMFDA and treated with 0.5 nM CMA or solvent control for 24 h. For each condition, 50,000 target cells were resuspended in fresh R10/50 without CMA with the corresponding number of effector CTLs to achieve the desired E:T ratio. Following the 4 h of coculture, the cells were stained with DAPI as a viability dye in addition to anti-PLAP and BB7.2 antibodies. Viable target cells were separated by gating for cells that were CellTracker Green-positive and excluded DAPI. The proportion of PLAP+ cells present in each condition was divided by that in the mean of target cells-only conditions (E:T=0:1) to report the proportion of PLAP+ cells surviving in the presence of CTLs. All samples were performed in experimental duplicates, except the target cells only conditions (E:T=0:1), which were performed in quadruplicate. Flow cytometry data were collected on a cytometer.

Figure 8:
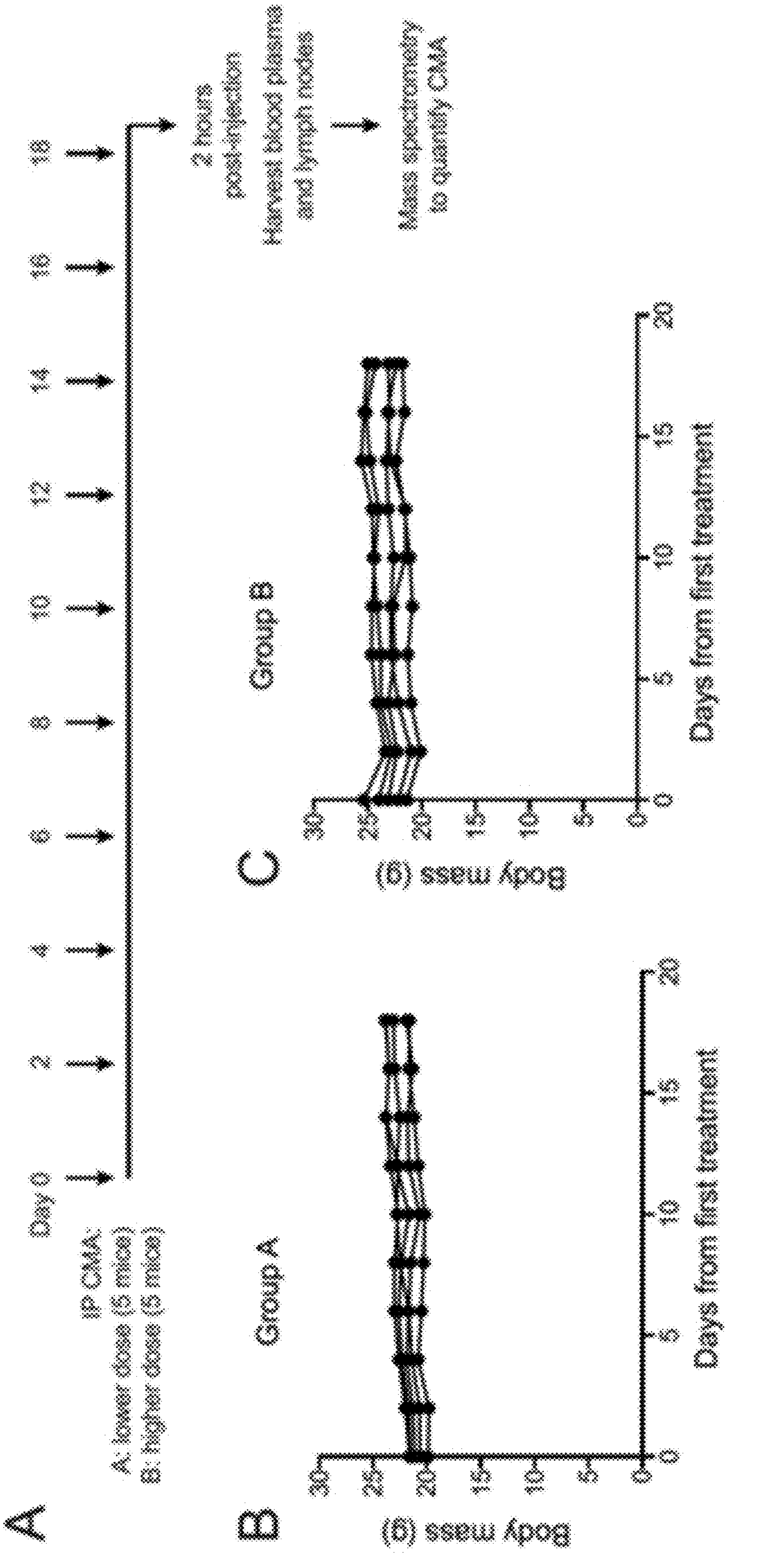
FIG. 8A is a schematic representation of experiments for FIG. 8B-D. Five mice per group received injections of CMA every 2 days for 10 doses. Blood plasma and lymph nodes were harvested from mice sacrificed 2 hours after the final injection.
FIG. 8B is a graph showing body mass as a function of days from first treatment for higher dose Group A. Mice were weighed prior to each dose of CMA and demonstrated no loss in body mass and no dose effect.
FIG. 8C is a graph showing body mass as a function of days from first treatment for lower dose Group B. Comparing higher (Group A) and lower (Group B) doses it can be seen that mice from both groups also showed no changes in behavior or fur (data not shown).
FIG. 8D is a summary graph of mass spectrometry data quantifying the concentration of CMA in blood plasma from mice in each Group A and Group B.
FIG. 8E is a summary graph of mass spectrometry data quantifying the concentration of CMA in lymph nodes from mice in each Group A and Group B. Points represent the 5 individual mice within each group. LOD=limit of detection. Open circles represent samples with CMA below the limit of detection.
FIG. 8F is a summary graph of flow cytometric data from experiments as in FIG. 1. Blood plasma was isolated from mice 30 minutes after injection with CMA, and CMA concentration was determined by mass spectrometry. Primary CD4+ T cells infected with HIV as in FIG. 1 were treated with 5% plasma from control mice spiked with known concentrations of CMA (standard curve) or with plasma from the CMA-injected mice diluted 1:20. Nef activity in cells receiving plasma from treated mice was compared to the standard curve based on the concentration of CMA as determined by mass spectrometry.
Figure 8:
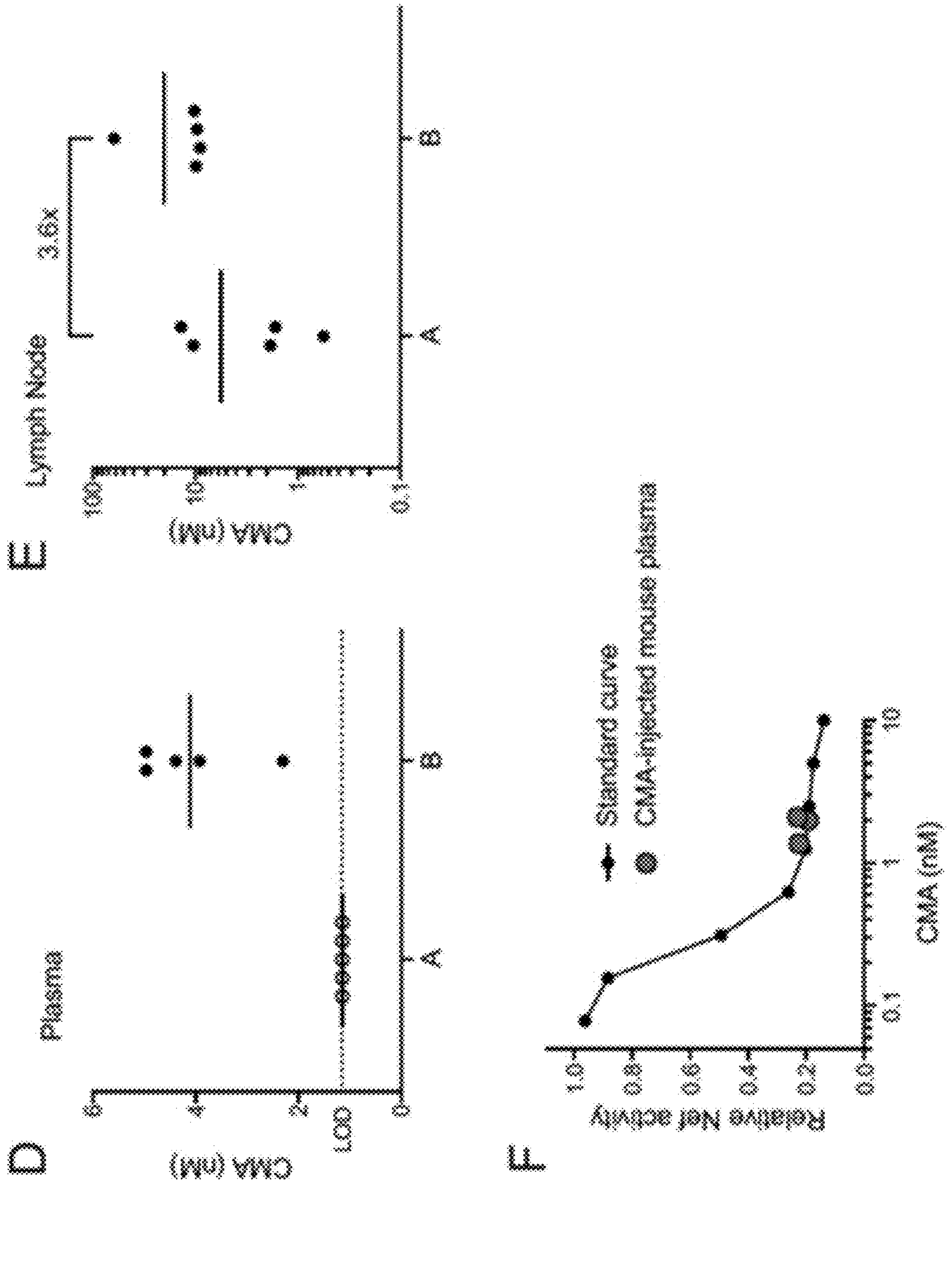

Mouse in vivo Assays. To further examine the tolerability of CMA, preliminary studies were performed in two groups of mice injected with different doses of CMA every other day for 18 days (FIG. 8A). Neither dose showed toxicity based on behavior, fur and weight loss (FIG. 8 B-C). An analysis of drug concentrations in plasma and lymph nodes performed 2 hours after the final dose confirmed that these dosing regimens attained levels of CMA higher than those required to counteract Nef activity in vitro (FIG. 8 D-E). In a separate experiment, plasma harvested from treated mice inhibited Nef in our in vitro assay (FIG. 8F). Taken together, these promising preliminary studies provide evidence that CMA is both efficacious and tolerable in vivo.

The use of the " a" or " an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict embodiments for purposes of illustration only. One of ordinary skill in the art will readily recognize from the following discussion that alternative embodiments of the structures and methods illustrated herein may be employed without departing from the principles described herein.

Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method of treating human immunodeficiency virus (HIV) infection in a patient in need thereof comprising administering to the patient a pharmaceutically-effective amount of a compound having a structure of Formula (I), or a pharmaceutically acceptable salt thereof:

(I)

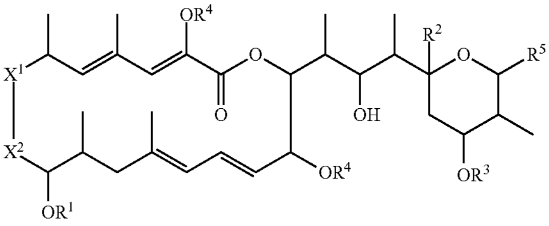

wherein

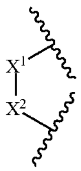
is
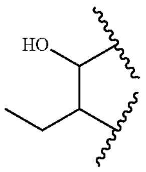

or represents a direct bond;

$R^1$ is H, C(O)$R^6$, or a sugar moiety;

$R^2$ is H or OH;

$R^3$ is H, C(O)$R^7$ or a sugar moiety;

each $R^4$ is independently H or $C_{1-6}$alkyl;

$R^5$ is $C_{1-6}$alkyl or $C_{2-6}$alkenyl; and $R^6$ and $R^7$ are each independently $C_{1-6}$ alkyl.

2. The method of claim 1, wherein the HIV infection is HIV-1 infection.

3. The method of claim 2, wherein the HIV-1 infection is infection with HIV subtype A, B, C, D, F, G, H, J, K, L, or a recombination thereof.

4. The method of claim 1, wherein treating HIV infection comprises reducing or eliminating an HIV reservoir in a host.

5. The method of claim 1, wherein the compound has a structure of Formula (Ia) or (Ib):

(Ia)

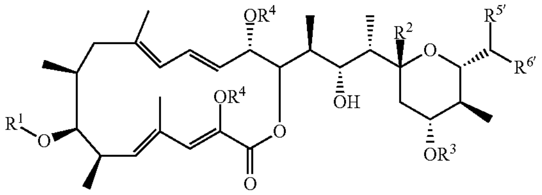

or (Ib)

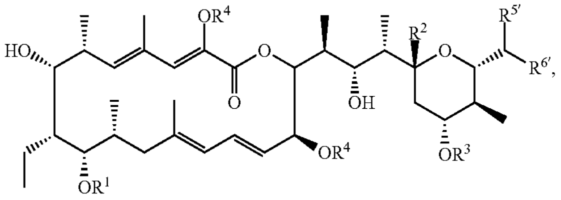

wherein $R^{5'}$ is $C_{1-5}$alkyl or $C_{2-5}$alkenyl and $R^{6'}$ is $C_{1-5}$alkyl.

6. The method of claim 5, wherein $R^{5'}$ is $C_{2-5}$alkenyl and $R^{6'}$ is H.

7. The method of claim 5, wherein $R^{5'}$ and $R^{6'}$ are methyl.

8. The method of claim 1, wherein $R^1$ is H.

9. The method of claim 1, wherein $R^2$ is H.

10. The method of claim 1, wherein $R^3$ is a sugar.

11. The method of claim 1, wherein $R^3$ is a carbamoyl sugar.

12. The method of claim 11, wherein $R^3$ is

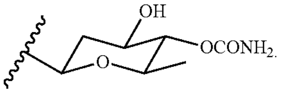

13. The method of claim 12, wherein at least one $R^4$ is $C_{1-6}$alkyl.

14. The method of claim 13, wherein at least one $R^4$ is methyl.

15. The method of claim 14, wherein each $R^4$ is methyl.

16. The method of claim 12, wherein each $R^4$ is $C_{1-6}$alkyl.

17. A method of treating human immunodeficiency virus (HIV) infection comprising administering to a patient in need thereof a pharmaceutically-effective amount of a compound, or pharmaceutically acceptable salt thereof, having a structure as shown in Table A:

TABLE A

| Compound No. | Structure |
|---|---|
| A1 | 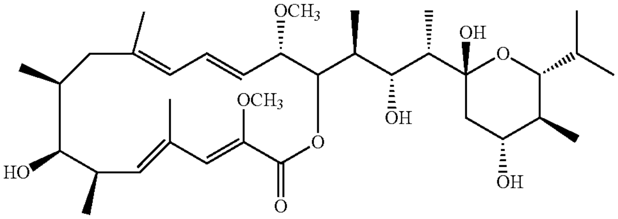 [SMILES: CO/C1=C\C(C)=C\[C@@H](C)[C@@H](O)[C@@H](C)C/C(C)=C/C=C/[C@H](OC)C([C@@H](C)[C@@H](O)[C@H](C)[C@@]2(O)C[C@@H](O)[C@H](C)[C@@H](C(C)C)O2)OC1=O] |
| A2 | 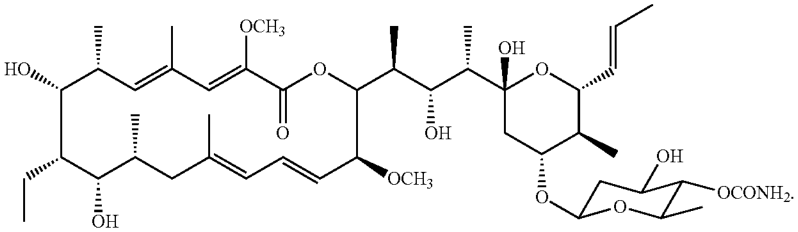 |

18. The method of claim 17, wherein the compound of Table A is in the form of a salt.

* * * * *